United States Patent
Hakamata

(10) Patent No.: US 6,597,439 B1
(45) Date of Patent: Jul. 22, 2003

(54) METHOD AND APPARATUS FOR MEASUREMENT OF LIGHT FROM ILLUMINATED SPECIMEN ELIMINATING INFLUENCE OF BACKGROUND LIGHT

(75) Inventor: Kazuo Hakamata, Kaisei-machi (JP)

(73) Assignee: Fuji Photo Film Co., Ltd., Kanagawa-Ken (JP)

( * ) Notice: Subject to any disclaimer, the term of this patent is extended or adjusted under 35 U.S.C. 154(b) by 0 days.

(21) Appl. No.: 09/502,579

(22) Filed: Feb. 11, 2000

(30) Foreign Application Priority Data

Feb. 12, 1999 (JP) .......................................... 11-033741
Aug. 26, 1999 (JP) .......................................... 11-239095

(51) Int. Cl.⁷ ............................................. G01N 21/00
(52) U.S. Cl. ........................................ 356/73; 356/218
(58) Field of Search .......................... 356/73, 218, 445, 356/447, 432, 433

(56) References Cited

U.S. PATENT DOCUMENTS

| | | | |
|---|---|---|---|
| 3,903,422 A | | 9/1975 | Buhrer |
| 4,291,979 A | * | 9/1981 | Yuasa et al. ................. 356/218 |
| 4,500,205 A | * | 2/1985 | Watanabe ................... 356/325 |
| 5,644,385 A | * | 7/1997 | Mizuno ..................... 356/3.04 |
| 5,800,348 A | * | 9/1998 | Kaestle ....................... 600/322 |
| 5,885,213 A | * | 3/1999 | Richardson et al. ........ 600/336 |
| 6,122,042 A | * | 9/2000 | Wunderman et al. ......... 356/73 |

FOREIGN PATENT DOCUMENTS

| | | |
|---|---|---|
| EP | 0 361 904 A2 | 4/1990 |
| EP | 0 383 244 A1 | 8/1990 |
| EP | 0 483 117 A2 | 4/1992 |
| WO | WO 97/08523 A1 | 3/1997 |

* cited by examiner

Primary Examiner—Frank G. Font
Assistant Examiner—Roy M. Punnoose
(74) Attorney, Agent, or Firm—Sughrue Mion, PLLC

(57) ABSTRACT

A method and an apparatus for performing measurement of light from an illuminated specimen, under background light having intensity which varies cyclically with a period. A first measuring operation is performed for a certain length of time while illuminating the specimen. Then, a second measuring operation is performed for the same length of time as the first operation without the illumination of the specimen. A result of measurement unaffected by the background light is obtained by subtracting a result of the second measuring operation from a result of the first measuring operation. The difference between beginning times of the first and second measuring operations is made equal to an integer multiple of the above period. Alternatively, the above length of time of each of the first and second operations is made equal to an integer multiple of the above period.

30 Claims, 12 Drawing Sheets

F I G. 1
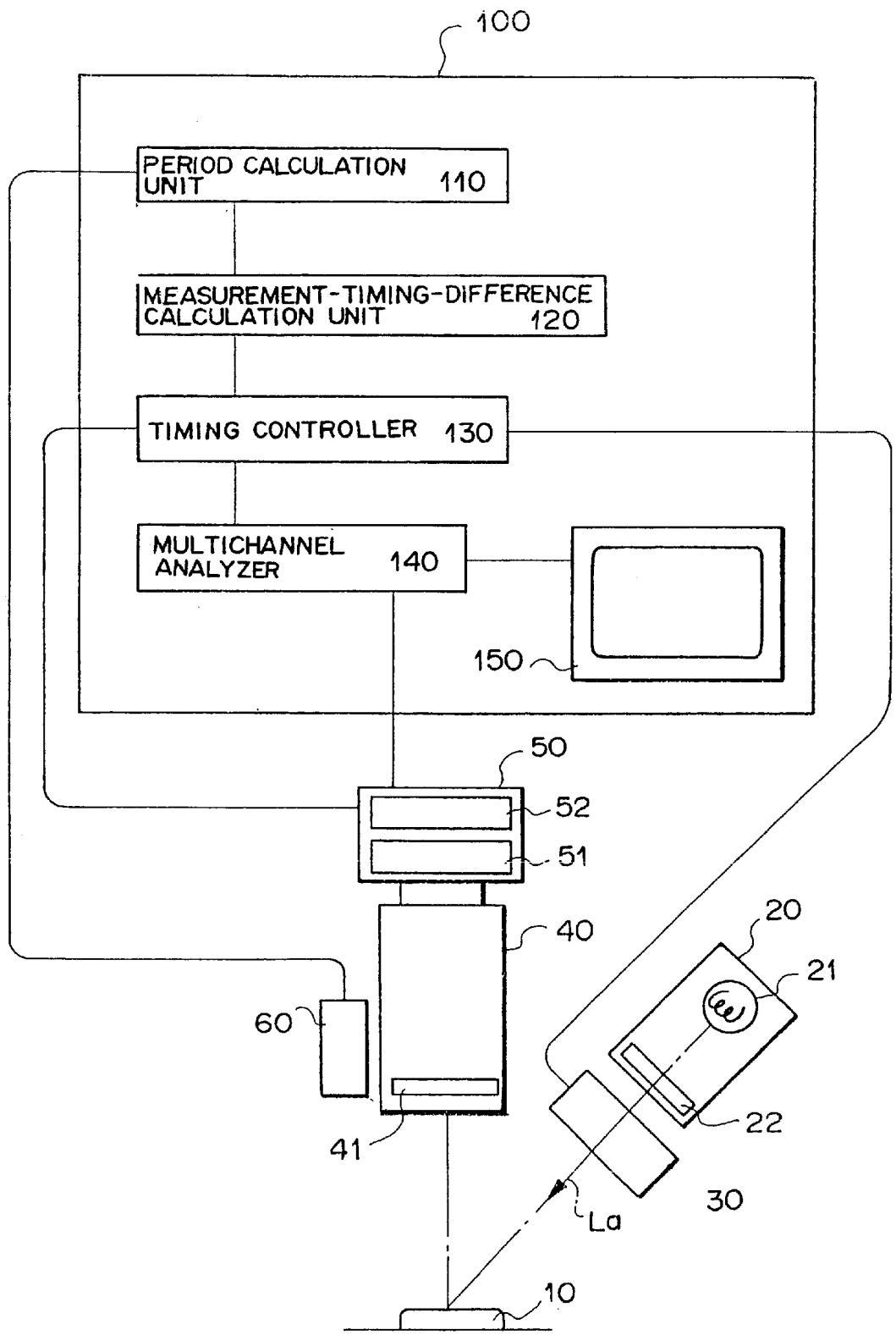

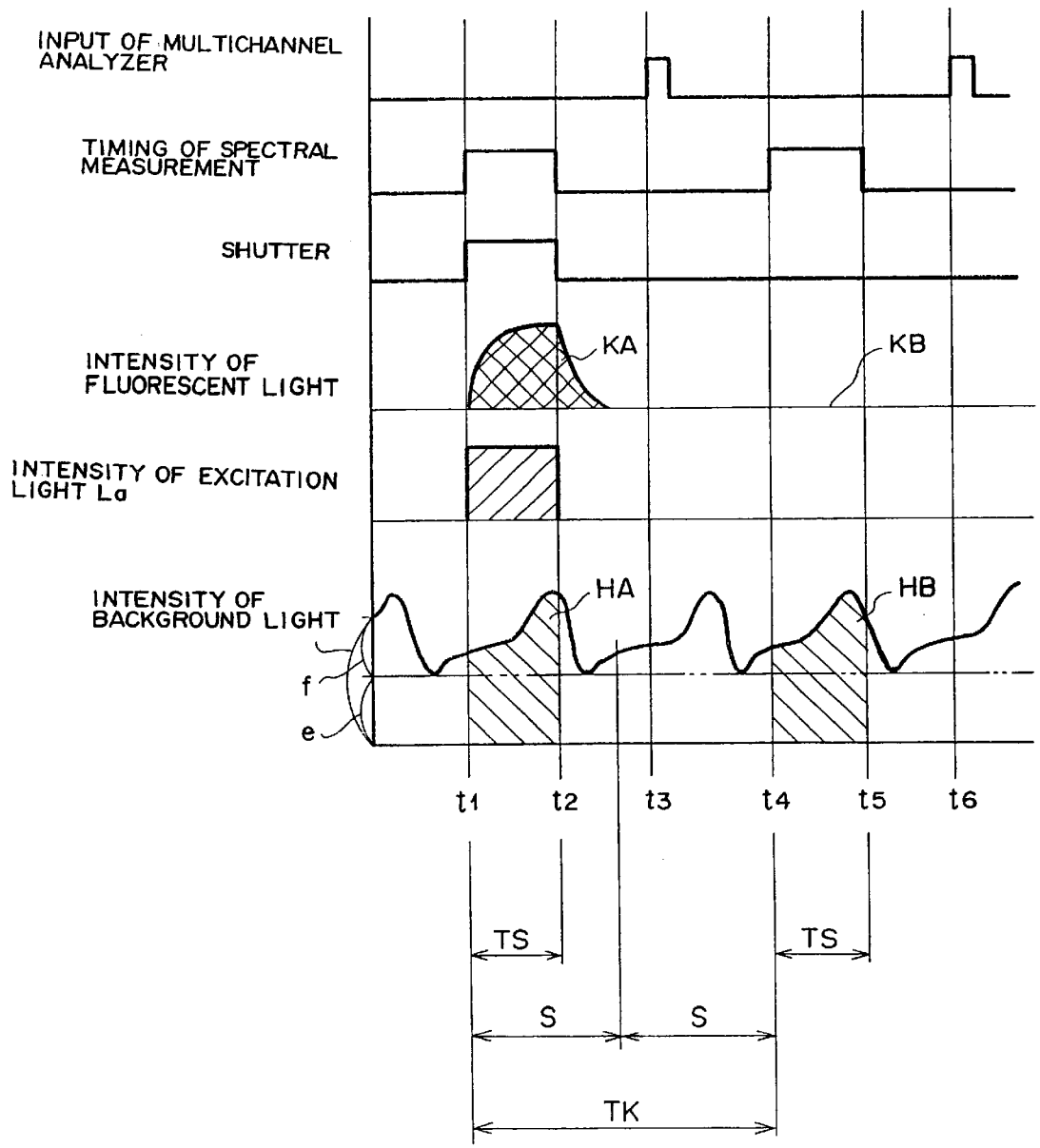

F I G . 6
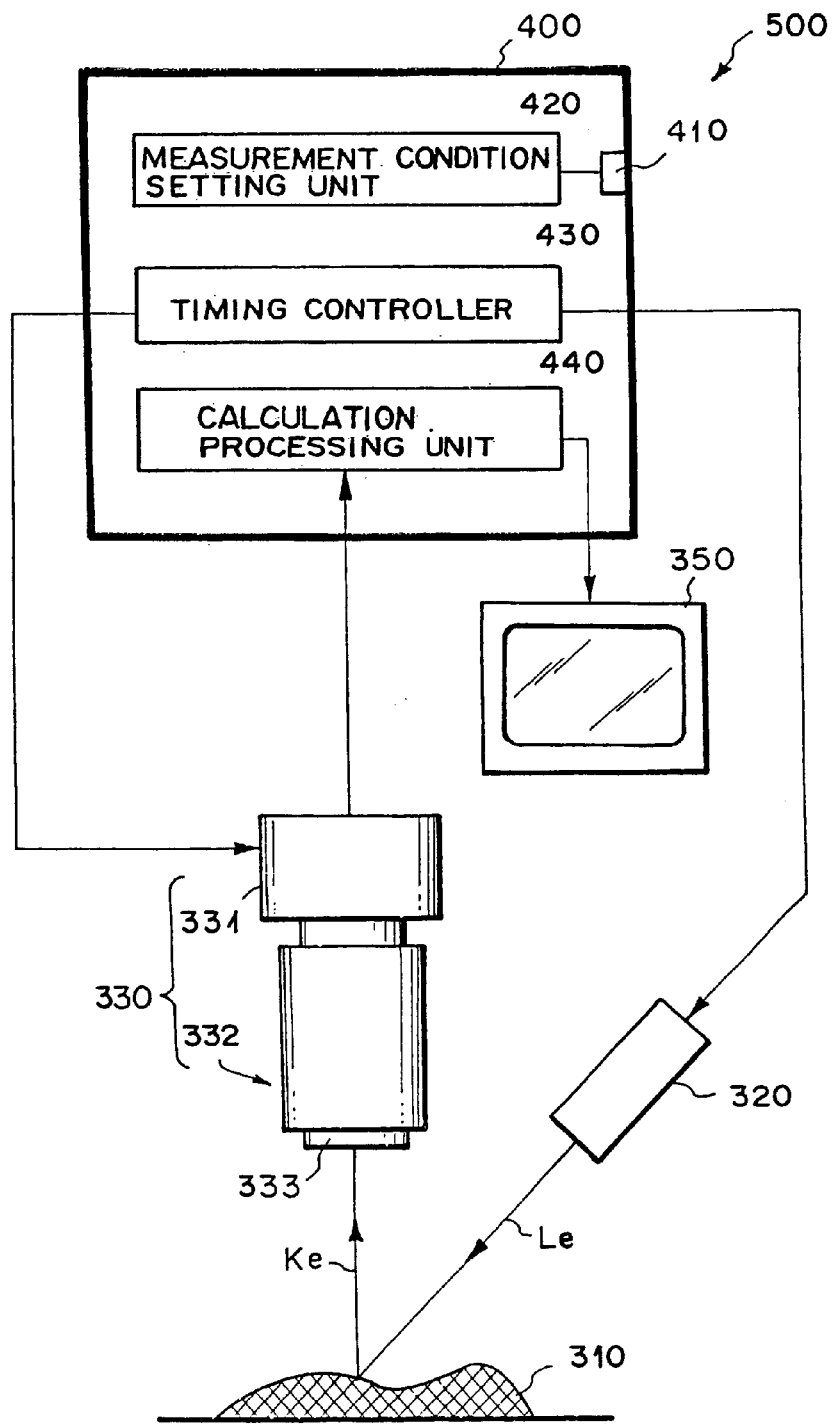

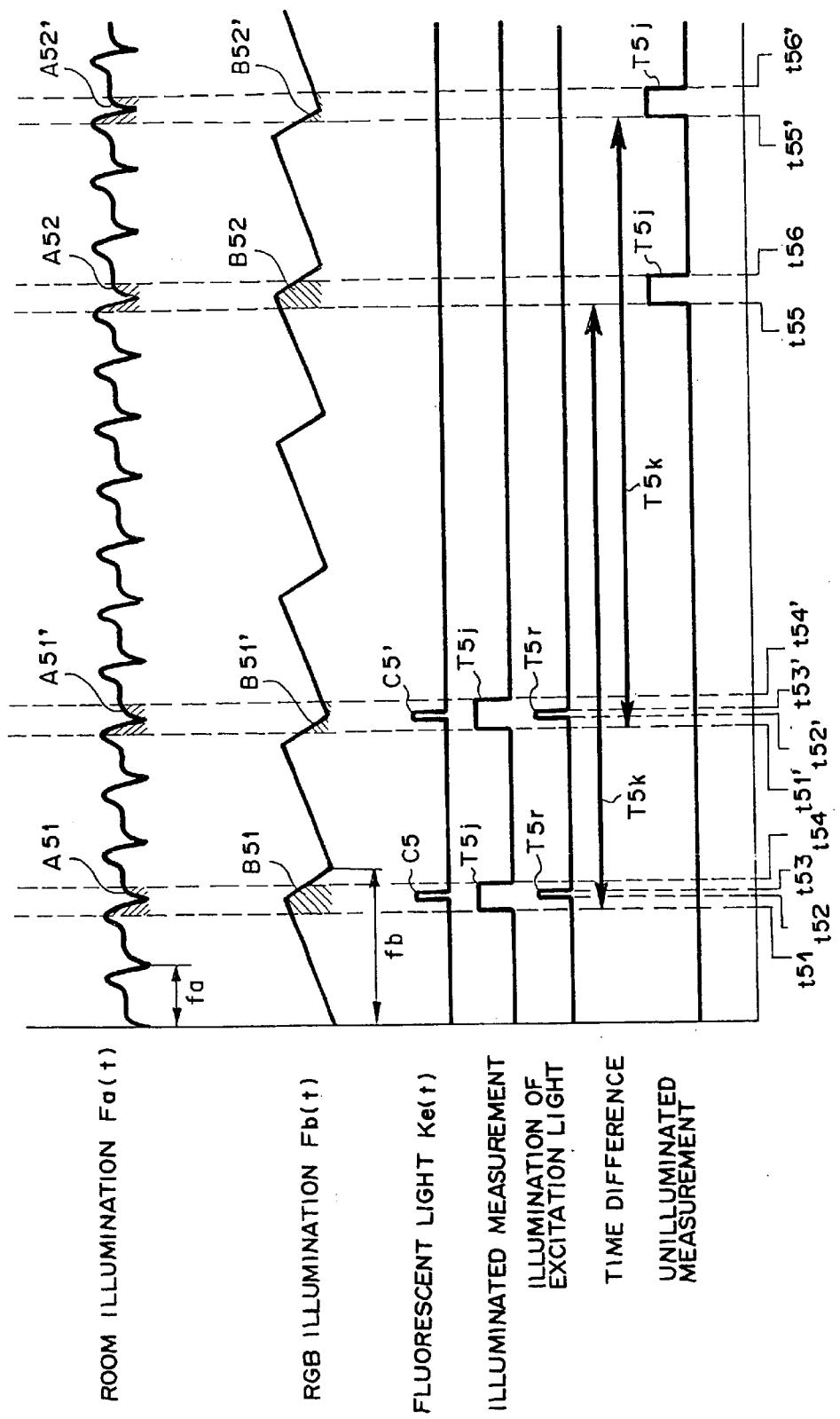

METHOD AND APPARATUS FOR MEASUREMENT OF LIGHT FROM ILLUMINATED SPECIMEN ELIMINATING INFLUENCE OF BACKGROUND LIGHT

BACKGROUND OF THE INVENTION

1. Field of the Invention

The present invention relates to an optical measurement method and an optical measurement apparatus for performing measurement of light which has been emitted from a specimen in response to illumination of the specimen, or has been reflected by or has penetrated through a specimen when the specimen is illuminated, under a condition that background light behaves as background noise. The background light is caused, for example, by room illumination.

2. Description of the Related Art

An optical measurement apparatus performing measurement of light as described above is conventionally known. In such an apparatus, it is not possible to perform precise measurement when light to be measured is incident on an optical detector together with room illumination light and other light from outside as background noise. Therefore, in a conventional technique, the background light is eliminated by an attenuation filter or a spatial filter before the background light is incident on the optical detector, where the attenuation filter attenuates light intensity in a specific wavelength range, and the spatial filter utilizes a pinhole.

Nevertheless, when using the above attenuation filter or spatial filter, it is not possible to separate the light to be measured from the background light when the wavelength range of the background light overlaps the wavelength range of the light to be measured. That is, a portion of the background light is mixed into the light to be measured and the quality of measurement deteriorates.

Alternatively, a technique of shortening an exposure time is proposed. In the technique, the exposure time is made so short, for example, not longer than 100 nsec, that the background light does not affect measurement data. In order to shorten the exposure time to not longer than 100 nsec, a short-pulse light source and a high-speed, high-sensitivity detector (e.g., an image intensifier) are necessary. However, these components are expensive, and therefore increase the manufacturing cost of the measurement apparatus. From the viewpoint of cost reduction, it is not possible to use such expensive components. On the other hand, the exposure time cannot be shortened to less then one micrometer when an inexpensive laser diode and charge-coupled device (CCD) are used. That is, the influence of the background light cannot be eliminated by use of the inexpensive laser diode and charge-coupled device (CCD). Further, even if the laser diode is driven to emit a short-pulse beam and the image intensifier is used for detection, it is not possible to obtain a high peak with a usual operation of driving the laser diode. That is, sufficient exposure energy cannot be supplied to a specimen with the above construction.

SUMMARY OF THE INVENTION

The first object of the present invention is to provide an optical measurement method and an optical measurement apparatus which can perform measurement of light with high accuracy even when the wavelength range of the background light overlaps the wavelength range of the light to be measured, which has been emitted from a specimen, or has been reflected by or has penetrated through a specimen when the specimen is illuminated.

The second object of the present invention is to provide an optical measurement method and an optical measurement apparatus enabling precise measurement of light which has been emitted from a specimen, or has been reflected by or has penetrated through a specimen when the specimen is illuminated, under a plurality of types of background light respectively having a plurality of different periods of cyclic intensity variations.

In order to accomplish the above-mentioned first object, according to the first aspect of the present invention, there is provided an optical measurement method for performing measurement of first light, which has been emitted from or reflected by a specimen, or has penetrated through the specimen, under background light having an intensity which varies cyclically with a period. The method contains steps of: (a) performing a first operation of measuring the first light for a first duration beginning at a first time, while illuminating the specimen with second light, to obtain a first measurement result; (b) performing a second operation of measuring the first light for a second duration having the same length as the first duration and beginning at a second time which is different from the first time by an integer multiple of the above period, while illumination of the specimen is stopped, to obtain a second measurement result; and (c) subtracting the second measurement result from the first measurement result, to obtain a third measurement result which is not affected by the background light.

In order to accomplish the above-mentioned first object, according to the second aspect of the present invention, there is provided an optical measurement apparatus for performing measurement of first light, which has been emitted from or reflected by a specimen, or has penetrated through the specimen, under background light having intensity which varies cyclically with a period. The apparatus contains a first measurement unit which performs a first operation of measuring the first light while illuminating the specimen by second light, to obtain a first measurement result; a second measurement unit which performs a second operation of measuring the first light while illumination of the specimen is stopped, to obtain a second measurement result; a control unit which controls timing of the operations of the first and second measurement units so that the first operation is performed for a first duration beginning at a first time, and the second operation is performed for a second duration having the same length as the first duration and beginning at a second time which is different from the first time by an integer multiple of the above period; and a calculation unit which obtains a third measurement result, which is not affected by the background light, by subtracting the second measurement result from the first measurement result.

According to the first and second aspects of the present invention, the difference between the beginning times of the first and second operations of measuring the first light is an integer multiple of the period of the cyclic variation of the intensity of the background light, and the first and second operations are performed for the same length of time. Since the specimen is not illuminated with the second light during the second operation, it is considered that an amount of influence by the background light included in the first measurement result of the first operation will be the same as the amount of the second measurement result of the second operation. Therefore, it is expected that the amount of influence by the background light included in the first measurement result of the first operation will be removed by subtracting the amount of the second measurement result of the second operation from the amount of the first result of the first operation. Thus, a final (third) measurement result can be obtained with high accuracy even when the wavelength range of the background light overlaps the wavelength range of the light to be measured, which has been emitted from a specimen in response to illumination of the specimen, or has been reflected by or has penetrated through a specimen when the specimen is illuminated.

In order to accomplish the above-mentioned first object, according to the third aspect of the present invention, there is provided an optical measurement method for performing measurement of first light, which has been emitted from or reflected by a specimen, or has penetrated through the specimen, under background light having an intensity which varies cyclically with a period. The method contains steps of: (a) performing a first operation of measuring the first light for a first duration having a length equal to an integer multiple of the above period, while illuminating the specimen by second light, to obtain a first measurement result; (b) performing a second operation of measuring the first light for a second duration having a length equal to the length of the first duration, while illumination of the specimen is stopped, to obtain a second measurement result; and (c) subtracting the second measurement result from the first measurement result, to obtain a third measurement result which is not affected by the background light.

In order to accomplish the above-mentioned first object, according to the fourth aspect of the present invention, there is provided an optical measurement apparatus for performing measurement of first light, which has been emitted from or reflected by a specimen, or has penetrated through the specimen, under background light having an intensity which varies cyclically with a period. The apparatus contains a first measurement unit which performs a first operation of measuring the first light while illuminating the specimen with second light to obtain a first measurement result; a second measurement unit which performs a second operation of measuring the first light while illumination of the specimen is stopped, to obtain a second measurement result; and a control unit which controls timing of the operations of the first and second measurement units so that each of the first and second operations is performed for a duration having an identical length equal to an integer multiple of the above period; and a calculation unit which obtains a third measurement result, which is not affected by the background light, by subtracting the second measurement result from the first measurement result.

According to the third and fourth aspects of the present invention, the first and second operations are also performed for the same length of time, and the length is equal to an integer multiple of the above period of the cyclic variation of the intensity of the background light. It is expected that an amount of influence by the background light on a measuring operation for an identical length of time will not change regardless of the beginning time of the measuring operation, when the length of time is equal to an integer multiple of the above period of the cyclic variation of the intensity of the background light. Since the specimen is not illuminated by the second light during the second operation, regardless of the beginning times of the first and second operations, it is expected that an amount of influence by the background light included in the first measurement result of the first operation will be the same as the amount of the second measurement result of the second operation. Therefore, it is expected that the amount of influence by the background light included in the first measurement result of the first operation will be removed by subtracting the amount of the second measurement result of the second operation from the amount of the first measurement result of the first operation. Thus, a final measurement result can be obtained with high accuracy even when the wavelength range of the background light overlaps the wavelength range of the light to be measured, which has been emitted from a specimen in response to illumination of the specimen, or has been reflected by or has penetrated through a specimen when the specimen is illuminated.

In the above first to fourth aspects of the present invention, the period may be obtained by measuring the intensity of the background light. When the period obtained based on the measured intensity of the background light is used for controlling the timing of the measurement operations in the present invention, an accurate value of the period can be used, and therefore the measurement can be performed with higher accuracy.

In addition, in the above first to fourth aspects of the present invention, each of the first and second operations may or may not be performed in synchronization with the cyclic variation of the background light.

Further, the above-mentioned "first light which has been emitted from a specimen" may be reradiation light such as fluorescent light, Raman scattering light, phosphorescent light, or the like.

The above-mentioned "first light, which has been "reflected by a specimen" may be light which has been polarized due to the reflection, or has a spectrum not containing a portion of components which has been absorbed by the specimen, or has intensity reduced due to the reflection in accordance with reflectance of the specimen, or has been changed by any combination of polarization, absorption of a spectrum component, and intensity reduction.

The above-mentioned "first light, which has penetrated through the specimen" may be light which has been polarized during the penetration, or has a spectrum not containing a portion of components which is absorbed by the specimen during the penetration, or has intensity reduced during the penetration in accordance with transmittance of the specimen, or has been changed by any combination of polarization, absorption of a spectrum component, and intensity reduction.

The above-mentioned "measurement of light" may include spectrum measurement of light and quantitative or qualitative measurement of intensity of light, and the measurement may be performed at one measurement point or at a number of measurement points. For example, the measurement may be performed by obtaining information on an image containing the measurement points, where such an image may be obtained by using a charge-coupled device (CCD).

In order to accomplish the above-mentioned second object, according to the fifth aspect of the present invention, there is provided an optical measurement method for performing measurement of first light, which has been emitted from or reflected by a specimen, or has penetrated through the specimen, under a plurality of types of background light respectively having a plurality of different periods with which intensities of the plurality of types of background light vary cyclically. The method contains steps of: (a) performing a first operation of measuring the first light for a first duration having a length equal to an integer multiple of the least common multiple of the plurality of different periods, while illuminating the specimen with second light, to obtain a first measurement result; (b) performing a second operation of measuring the first light for a second duration having a length equal to the length of the first duration, while illumination of the specimen is stopped, to obtain a second measurement result; and (c) subtracting the second measurement result from the first measurement result, to obtain a third measurement result which is not affected by the plurality of types of background light.

In order to accomplish the above-mentioned second object, according to the sixth aspect of the present invention, there is provided an optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically. The apparatus contains a first measurement unit which performs a first operation of measuring the first light while illuminating the specimen with second light, to obtain a first measurement result; a second measurement unit which performs a second operation of measuring the first light while illumination of the specimen is stopped, to obtain a second measurement result; a control unit which controls timing of the operations of the first and second measurement units so that each of the first and second operations is performed for a duration having an identical length equal to an integer multiple of the least common multiple of the plurality of different periods; and a calculation unit which obtains a third measurement result, which is not affected by the plurality of types of background light, by subtracting the second measurement result from the first measurement result.

According to the fifth and sixth aspects of the present invention, the first and second operations are performed for the same length of time, and the length is equal to an integer multiple of the least common multiple of the plurality of different periods of the cyclic variations of the intensities of the plurality of types of background light. It is expected that an amount of influence of the plurality of types of background light on a measuring operation for an identical length of time will not change regardless of the beginning time of the measuring operation, when the length of time is equal to an integer multiple of the least common multiple of the plurality of different periods of the cyclic variations of the intensities of the plurality of types of background light. Since the specimen is not illuminated with the second light during the second operation, regardless of the beginning times of the first and second operations, it is expected that an amount of influence of the plurality of types of background light included in the first measurement result of the first operation will be the same as the amount of the second measurement result of the second operation. Therefore, it is expected that the influence of the plurality of types of background light included in the first measurement result of the first operation will be removed by subtracting the amount of the second measurement result of the second operation from the amount of the first measurement result of the first operation. Thus, a final measurement result can be obtained with high accuracy even when the wavelength ranges of the plurality of types of background light overlap the wavelength range of the light to be measured, which has been emitted from a specimen in response to illumination of the specimen, or has been reflected by or has penetrated through a specimen when the specimen is illuminated.

In order to accomplish the above-mentioned second object, according to the seventh aspect of the present invention, there is provided an optical measurement method for performing measurement of first light, which has been emitted from or reflected by a specimen, or has penetrated through the specimen, under a plurality of types of background light respectively having a plurality of different periods with which intensities of the plurality of types of background light vary cyclically. The method contains steps of: (a) performing a first operation of measuring the first light for a first duration beginning at a first time, while illuminating the specimen with second light, to obtain a first measurement result; (b) performing a second operation of measuring the first light for a second duration having the same length as the first duration and beginning at a second time which is different from the first time by an integer multiple of the least common multiple of the plurality of different periods, while illumination of the specimen is stopped, to obtain a second measurement result; and (c) subtracting the second measurement result from the first measurement result, to obtain a third measurement result which is not affected by the plurality of types of background light.

In order to accomplish the above-mentioned second object, according to the eighth aspect of the present invention, there is provided an optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically. The apparatus contains a first measurement unit which performs a first operation of measuring the first light while illuminating the specimen with second light, to obtain a first measurement result; a second measurement unit which performs a second operation of measuring the first light while illumination of the specimen is stopped, to obtain a second measurement result; a control unit which controls timing of the operations of the first and second measurement units so that the first operation is performed for a first duration beginning at a first time, and the second operation is performed for a second duration having the same length as the first duration and beginning at a second time which is different from the first time by an integer multiple of the least common multiple of the plurality of different periods; and a calculation unit which obtains a third measurement result, which is not affected by the plurality of types of background light, by subtracting the second measurement result from the first measurement result.

Preferably, the optical measurement method according to the seventh aspect of the present invention, or in the optical measurement apparatus according to the eighth aspect of the present invention may have the following additional features (i) to (iv).

(i) Each of the first and second operations may be performed a plurality of times.

(ii) Each of the first and second operations may be performed in synchronization with one of the plurality of different periods of a selected one of the plurality of types of background light.

(iii) In addition to the features of (i) and (ii), each of the first and second operations may be performed in the vicinity of a certain phase of the one of the plurality of different periods, where the intensity of the selected one of the plurality of types of background light is minimized in the certain phase.

(iv) In addition to the features of (i) and (ii), the one of the plurality of different periods may be the minimum period among the plurality of different periods.

According to the seventh and eighth aspects of the present invention, the difference between the beginning times of the first and second operations of measuring the first light is an integer multiple of the least common multiple of the plurality of different periods of the cyclic variations of the intensities of the plurality of types of background light, and the first and second operations are performed for the same length of time. Since the specimen is not illuminated by the second light during the second operation, it is considered that the amount of influence of the plurality of types of background light included in the first measurement result of the first operation will be the same as the amount of the second measurement result of the second operation. Therefore, it is expected that the influence of the plurality of types of background light included in the first measurement result of the first operation will be removed by subtracting the amount of the second measurement result of the second operation from the amount of the first result of the first operation. Thus, a final (third) measurement result can be obtained with high accuracy even when the wavelength ranges of the plurality of types of background light overlap the wavelength range of the light to be measured, which has been emitted from a specimen in response to illumination of the specimen, or has been reflected by or has penetrated through a specimen when the specimen is illuminated.

In order to accomplish the above-mentioned second object, according to the ninth aspect of the present invention, there is provided an optical measurement method for performing measurement of first light, which has been emitted from or reflected by a specimen, or has penetrated through the specimen, under a plurality of types of background light respectively having a plurality of different periods with which intensities of the plurality of types of background light vary cyclically. The method contains steps of: (a) performing a first operation of measuring the first light for a first duration beginning at a first time and having a length equal to an integer multiple of the least common multiple of at least one period among the plurality of different periods, while illuminating the specimen with second light, to obtain a first measurement result; (b) performing a second operation of measuring the first light for a second duration having the same length as the first duration and beginning at a second time which is different from the first time by an integer multiple of the least common multiple of the plurality of different periods other than the at least one period, while illumination of the specimen is stopped, to obtain a second measurement result; and (c) subtracting the second measurement result from the first measurement result, to obtain a third measurement result which is not affected by the plurality of types of background light.

In order to accomplish the above-mentioned second object, according to the tenth aspect of the present invention, there is provided an optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically. The apparatus contains a first measurement unit which performs a first operation of measuring the first light while illuminating the specimen with second light, to obtain a first measurement result; a second measurement unit which performs a second operation of measuring the first light while illumination of the specimen is stopped, to obtain a second measurement result; a control unit which controls timing of the operations of the first and second measurement units so that the first operation is performed for a first duration beginning at a first time and having a length equal to an integer multiple of the least common multiple of at least one period among the plurality of different periods, and the second operation is performed for a second duration having the same length as the first duration and beginning at a second time which is different from the first time by an integer multiple of the least common multiple of the plurality of different periods other than the at least one period; and a calculation unit which obtains a third measurement result, which is not affected by the plurality of types of background light, by subtracting the second measurement result from the first measurement result.

When the number of the at least one period is one in the optical measurement method according to the ninth aspect of the present invention, and in the optical measurement apparatus according to the tenth aspect of the present invention, the least common multiple of the at least one period is the one period per se.

Preferably, the optical measurement method according to the ninth aspect of the present invention, or in the optical measurement apparatus according to the tenth aspect of the present invention may have the following additional features (v) to (viii).

(v) Each of the first and second operations may be performed a plurality of times.

(vi) Each of the first and second operations may be performed in synchronization with a selected one of the plurality of different periods other than the at least one period.

(vii) In addition to the features of (v) and (vi), each of the first and second operations may be performed in the vicinity of a certain phase of the selected one of the plurality of different periods other than the at least one period, where the intensity of the selected one of the plurality of types of background light is minimized in the certain phase.

(viii) In addition to the features of (v) and (vi), the selected one of the plurality of different periods other than the at least one period may be the minimum period among the plurality of different periods other than the at least one period.

According to the ninth and tenth aspects of the present invention, the first and second operations are performed for the same length of time, and the length is equal to an integer multiple of the least common multiple of at least one period, among the plurality of different periods, of at least one cyclic variation of the intensity or intensities of at least one type of background light corresponding to the at least one period. It is expected that an amount of influence of the at least one type of background light on a measuring operation for an identical length of time will not change regardless of the beginning time of the measuring operation, when the length of time is equal to an integer multiple of the least common multiple of the at least one period of the at least one cyclic variation of the intensity or intensities of the at least one type of background light corresponding to the at least one period. Since the specimen is not illuminated with the second light during the second operation, regardless of the beginning times of the first and second operations, it is expected that an amount of influence by the at least one type of background light included in the first measurement result of the first operation will be the same as the amount of the second measurement result of the second operation. Therefore, it is expected that the amount of influence by the at least one type of background light included in the first measurement result of the first operation will be removed by subtracting the amount of the second measurement result of the second operation from the amount of the first measurement result of the first operation.

In addition, the difference between the beginning times of the first and second operations of measuring the first light is an integer multiple of the least common multiple of the rest of the plurality of different periods other than the at least one period, and the first and second operations are performed for the same length of time. Since the specimen is not illuminated by the second light during the second operation, it is considered that an amount of influence of the rest of the plurality of types of background light other than the abovementioned at least one type of background light corresponding to the rest of the plurality of different periods other than the at least one period, included in the first measurement result of the first operation, will be the same as the amount of a component of the second measurement result generated by the rest of the plurality of types of background light other than the at least one type of background light. Therefore, it is expected that the amount of influence of the rest of the plurality of types of background light other than the at least one type of background light, included in the first measurement result of the first operation, will be removed by subtracting the amount of the second measurement result of the second operation from the amount of the first result of the first operation.

Thus, it is expected that the amount of influence of all of the plurality of types of background light included in the first measurement result of the first operation will be removed by subtracting the amount of the second measurement result of the second operation from the amount of the first result of the first operation, and a final (third) measurement result can be obtained with high accuracy even when the wavelength range of the background light overlaps the wavelength range of the light to be measured, which has been emitted from a specimen in response to illumination of the specimen, or has been reflected by or has penetrated through a specimen when the specimen is illuminated.

Further, in the fifth to tenth aspects of the present invention, the plurality of types of background light means a plurality of types of background light which are required to be eliminated from the measurement result.

DESCRIPTION OF THE DRAWINGS

FIG. 1 is a diagram illustrating an outline of the construction of an optical measurement apparatus as a first embodiment of the present invention, provided for measuring a spectrum of fluorescent light.

FIG. 2 is a timing chart of spectrum measurement in the first embodiment.

FIG. 6 is a diagram illustrating an outline of a construction of an apparatus for measuring a spectrum of fluorescent light, which can be commonly used in the third, fourth, fifth, sixth, and seventh embodiments of the present invention.

FIG. 12 is a timing chart of the operations in the seventh embodiment, which realizes the fifth and fourth aspects of the present invention.

DESCRIPTION OF PREFERRED EMBODIMENTS

Figure 3A:
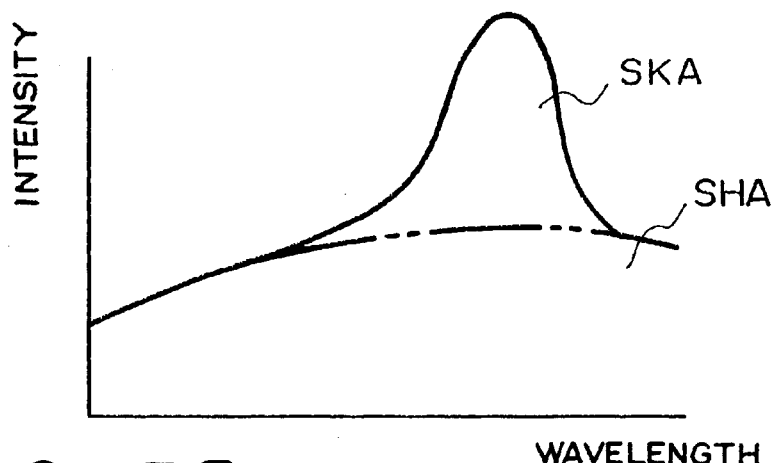
FIG. 3A shows a spectral distribution obtained by measurement when the specimen is illuminated.

Embodiments of the present invention are explained in detail below with reference to drawings.

First Embodiment

FIG. 1 is a diagram illustrating an outline of the construction of an apparatus for measuring a spectrum of fluorescent light, as a first embodiment of the present invention. The apparatus of FIG. 1 executes the method according to the first aspect of the present invention, and therefore realizes the apparatus according to the second aspect of the present invention.

The optical measurement apparatus as the first embodiment of the present invention contains a light source 20, a shutter 30, an optical condenser system 40, a spectrometer 50, an optical intensity measurement device 60, and a controller 100. The light source 20 emits an excitation light La for illuminating the specimen 10. The optical condenser system 40 condenses fluorescent light emitted from the specimen 10 in response to the illumination by the excitation light La. The spectrometer 50 obtains a spectrum of the fluorescent light condensed by the optical condenser system 40, and supplies measured values to the controller 100. The optical intensity measurement device 60 measures (variation of) intensity of background light, and supplies the measured values of the intensity to the controller 100. An optical path for the excitation light La emitted from the light source 20 is opened and closed by the shutter 30. The controller 100 controls operations of opening and closing the shutter 30 and starting and stopping the measurement.

The light source 20 contains a mercury vapor lamp 21 as an excitation light source and a band-pass filter 22 which is provided in the position of an outgoing window. The band-pass filter 22 passes a specific wavelength band of light. The optical condenser system 40 contains a long-wavelength-pass filter 41 which stops excitation light La reflected by the specimen 10, and passes the fluorescent light emitted from the specimen 10. Since the wavelength band of the fluorescent light is located on the longer-wavelength side of the excitation light La, the excitation light La can be stopped by the long-wavelength-pass filter 41. The spectrometer 50 contains a spectrally-dispersing portion 51 and light-measuring portion 52. The spectrally-dispersing portion 51 spectrally disperses the light condensed by the optical condenser system 40. The photometric portion 52 is constituted by, for example, a diode array, to detect intensities of respective spectral components of the light condensed by the optical condenser system 40, where the detected intensities of respective spectral components indicate a spectral distribution of the light.

The controller 100 contains a period calculation unit 110, a measurement-timing-difference calculation unit 120, a timing controller 130, a multichannel analyzer 140, and a display device 150.

The period calculation unit 110 receives the values measured by the optical intensity measurement device 60, which indicate the variation of the intensity of the background light, and obtains a value S indicating the period of the cyclic variation by calculation. The measurement-timing-difference calculation unit 120 receives the period value S obtained by the period calculation unit 110, and obtains a timing difference value TK determining a difference between timing of illuminated measurement and timing of unilluminated measurement by multiplying the period value by an integer, which is stored in advance in the measurement-timing-difference calculation unit 120. The illuminated measurement is measurement performed when the specimen 10 is illuminated by the excitation light La, and the unilluminated measurement is measurement performed when the specimen 10 is not illuminated by the excitation light La. The obtained timing difference value TK is supplied to the timing controller 130. The timing controller 130 controls the timing of the illuminated measurement and the unilluminated measurement, by outputting start control signals and stop control signals for the illuminated measurement and the unilluminated measurement to the spectrometer 50, the multichannel analyzer 140, and the shutter 30, based on the above timing difference value TK and a measurement time value TS, which is stored in advance in the timing controller 130. The timing controller 130 further outputs timing control signals to the multichannel analyzer 140. The multichannel analyzer 140 receives from the spectrometer 50 the intensity values indicating spectral distributions obtained by the illuminated measurement and the unilluminated measurement, based on the above timing control signals, and stores the received intensity values indicating spectral distributions, in the multichannel analyzer 140. Further, the multichannel analyzer 140 subtracts the intensity values indicating the spectral distribution of the unilluminated measurement from the intensity values indicating the spectral distribution of the illuminated measurement, and supplies the subtraction result to the display device 150.

Details of the operations of measuring a spectrum of fluorescent light by the apparatus of the first embodiment are explained below.

First, the operations of setting the timing difference value TK in the optical measurement apparatus are explained.

The mercury vapor lamp 21 constantly emits light, and the excitation light La passed through the band-pass filter 22 contains an emission line called as H line, having a center wavelength of 405 nm.

Before the measurement of the spectral distribution, the shutter 30 is closed, and therefore the excitation light La is stopped by the shutter 30. The optical intensity measurement device 60 performs the measurement of the intensity of the light and supplies the measurement result to the controller 100, before the measurement of the spectral distribution.

Since the shutter 30 is closed before the measurement of the spectral distribution, the optical intensity measurement device 60 measures the background light only, where the background light may be caused by, for example, room illumination. The measured intensity values of the light indicate the variation of the intensity of the background light. Based on the intensity values of the background light supplied to the controller 100, the period calculation unit 110 calculates the period value S. Then, the period S is multiplied by the aforementioned integer stored in the measurement-timing-difference calculation unit 120 to obtain the timing difference value TK. In this example, the integer is two. Therefore, TK=2S. The timing controller 130 stores the timing difference value TK as the difference between the timings of the illuminated measurement and the unilluminated measurement. Thus, the set-up operation of the timing difference value TK is completed.

Next, details of the operations of the illuminated measurement and the unilluminated measurement in the first embodiment are explained below.

The timing controller 130 stores in advance the length TS of the measurement time of each of the illuminated measurement and the unilluminated measurement. Based on the above timing difference value TK and the length TS of measurement time, the timing controller 130 outputs the start control signals and the stop control signals of the illuminated measurement and the unilluminated measurement to the spectrometer 50, the multichannel analyzer 140, and the shutter 30, as illustrated in FIG. 2. Thus, the illuminated measurement and the unilluminated measurement are performed in accordance with the start control signals and the stop control signals.

Referring to FIG. 2, when the illuminated measurement is started at time t1, the shutter 30 is opened, and the specimen 10 is illuminated by the excitation light La. In response to the illumination by the excitation light La, the specimen 10 emits fluorescent light. Also, at time t1, the spectrometer 50 starts the measurement. Thus, the fluorescent light KA emitted by the specimen 10 and the background light HA passed through the optical condenser system 40 are spectrally dispersed by the spectrally-dispersing portion 51, and the photometric portion 52 measures the intensities of the spectral components of the spectrally-dispersed light. At time t2, i.e., when time TS has elapsed after time t1, the illuminated measurement is stopped. That is, at time t2, the spectrometer 50 stops the measurement, and holds the measured intensities of the spectral components. Also the shutter 30 is closed to stop the illumination of the specimen 10 by the excitation light La. The above intensities obtained by the illuminated measurement, which indicate a sum of spectra of the background light HA and the fluorescent light KA, are supplied to and stored in the multichannel analyzer 140 at time t3.

At time t4, i.e., when time 2S has elapsed after time t1, the unilluminated measurement is started. That is, the spectrometer 50 starts the measurement of the intensities of the spectral components of the spectrally dispersed light. During the unilluminated measurement, the shutter 30 is closed. Since the specimen 10 is not illuminated by the excitation light La, the intensities KB of the fluorescent light is zero, and the spectrometer 50 measures the intensities of the background light HB only. At time t5, i.e., when time TS has elapsed after time t4, the unilluminated measurement is stopped. That is, the spectrometer 50 stops the measurement, and holds the measured intensities of the spectral components. The intensities obtained by the unilluminated measurement are supplied to and stored in the multichannel analyzer 140 at time t6.

Next, the operations of calculation and display of the spectral distributions in the first embodiment are explained below.

The multichannel analyzer 140 subtracts the intensity values indicating the spectral distribution HB obtained by the unilluminated measurement from the intensity values indicating the spectral distribution obtained by the illuminated measurement to obtain the spectral distribution of the fluorescent light KA, and supplies the calculation result to the display device 150.

Figure 3B:
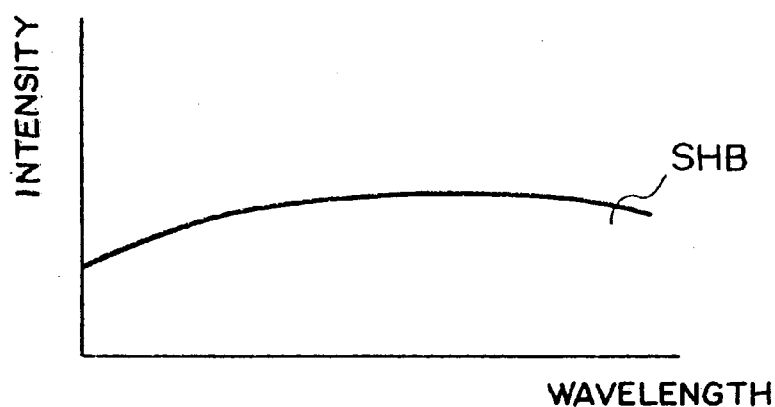
FIG. 3B shows a spectral distribution obtained by measurement when the specimen is not illuminated.
Figure 3C:
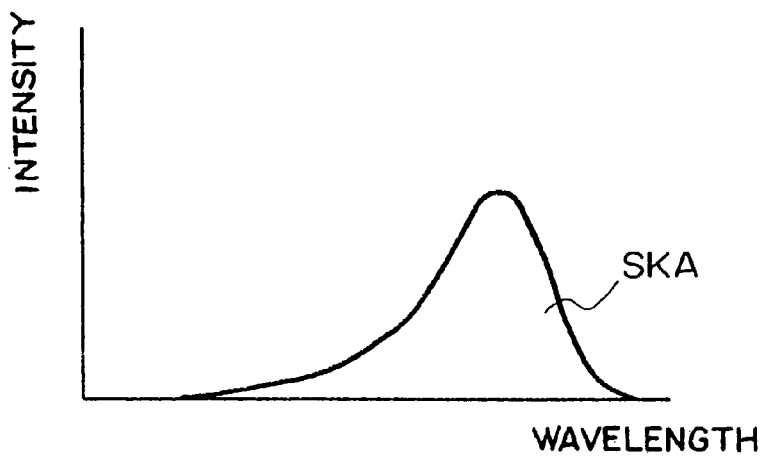
FIG. 3C shows a spectral distribution obtained by subtracting the spectral distribution of FIG. 3B from the spectral distribution of FIG. 3A.

FIG. 3A shows a spectral distribution obtained by the illuminated measurement, FIG. 3B shows a spectral distribution obtained by the unilluminated measurement, and FIG. 3C shows a spectral distribution obtained by subtracting the spectral distribution of FIG. 3B from the spectral distribution of FIG. 3A.

Since the illuminated measurement and the illuminated measurement are performed in the same phase interval in the cyclic variation of the intensity of the background light, the contribution SHA of the background light to the spectral distribution of the illuminated measurement illustrated in FIG. 3A is considered to be substantially identical to the spectral distribution SHB of the unilluminated measurement illustrated in FIG. 3B. Therefore, the spectral distribution SKA of the fluorescent light included in the illuminated measurement (as illustrated in FIG. 3C) can be obtained by subtracting the spectral distribution of FIG. 3B from the spectral distribution of FIG. 3A.

Then, the spectral distribution SKA of the fluorescent light obtained as above is displayed as an image by the display device 150.

As described above, by using the optical measurement apparatus of the first embodiment of the present invention, a spectrum of the light to be measured can be measured with high accuracy even when the wavelength range of the background light overlaps the wavelength range of the light to be measured, which has been emitted from a specimen in response to illumination of the specimen, or has been reflected by or has penetrated through a specimen when the specimen is illuminated.

Second Embodiment

Figure 4:
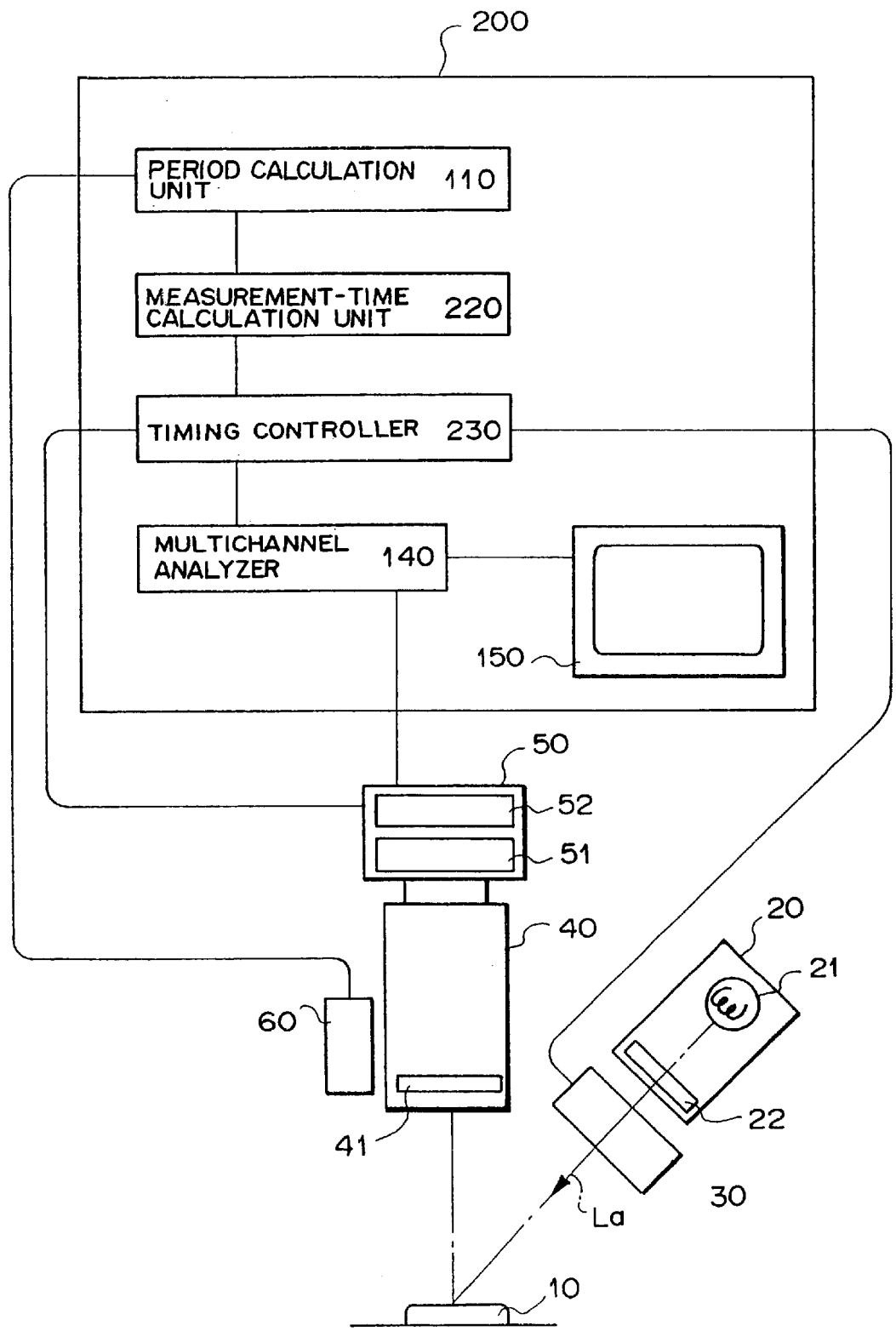
FIG. 4 is a diagram illustrating an outline of the construction of an optical measurement apparatus as a second embodiment of the present invention, provided for measuring a spectrum of fluorescent light.
Figure 5:
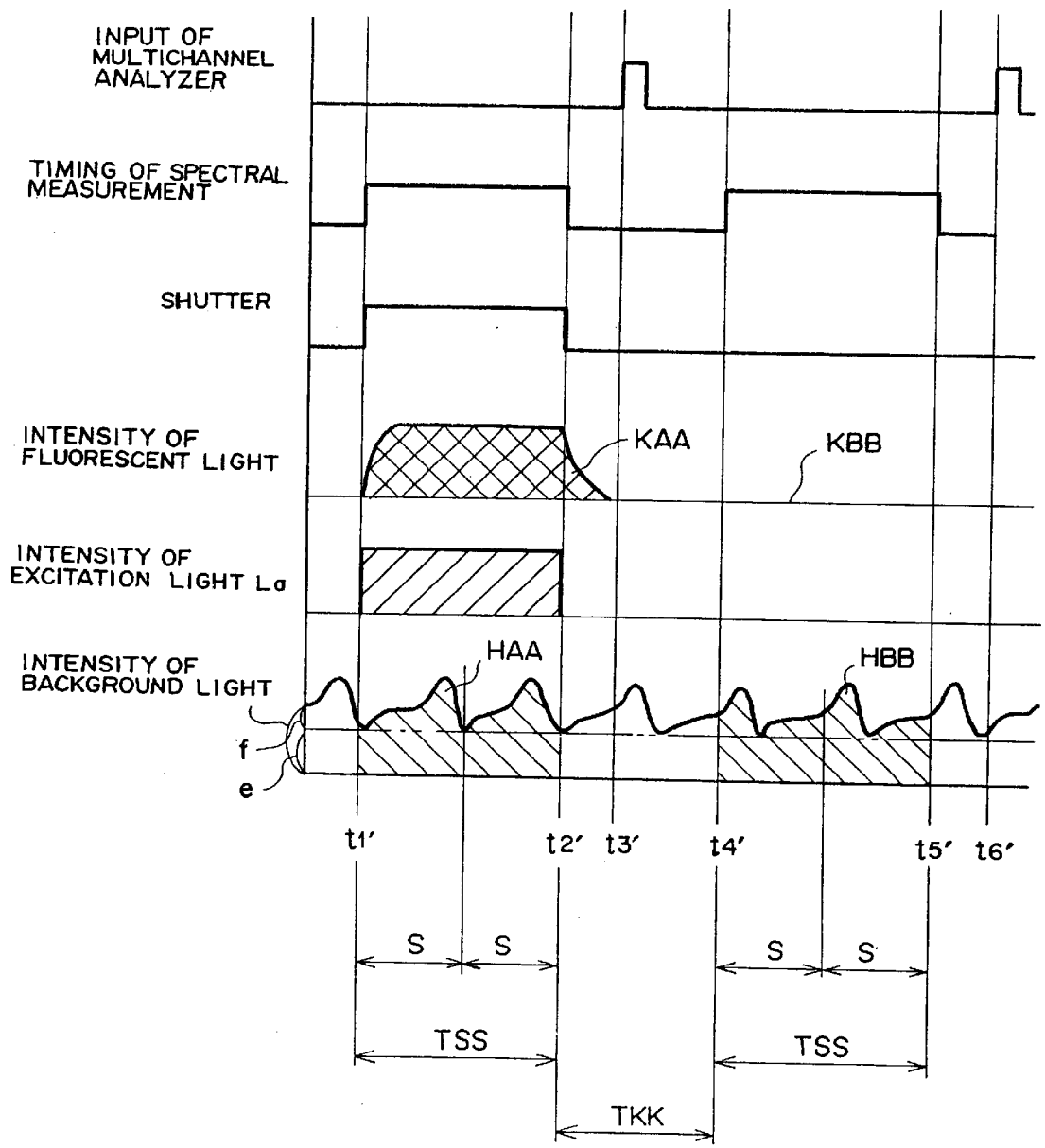
FIG. 5 is a timing chart of spectrum measurement in the second embodiment.

Next, explanations will be provided on an apparatus for measuring a spectral distribution of fluorescent light as a second embodiment of the present invention, with reference to FIGS. 4 and 5. Elements in FIG. 4 which have the same reference numerals as FIG. 1 function in the same way as the corresponding elements in FIG. 1. Therefore, the descriptions of those elements are not repeated here.

FIG. 4 shows an outline of the construction of an apparatus for measuring a spectrum of fluorescent light, as the second embodiment of the present invention. The apparatus of FIG. 4 executes the method according to the third aspect of the present invention, and therefore realizes the apparatus according to the fourth aspect of the present invention.

The controller 200 in the construction of FIG. 4 contains a period calculation unit 110, a measurement-time calculation unit 220, a timing controller 230, a multichannel analyzer 140, and a display device 150.

The period calculation unit 110 receives the intensity values measured by the optical intensity measurement device 60, which indicate the variation of the intensity of the background light, and obtains the value S indicating the period of the variation by calculation. The measurement-time calculation unit 220 receives the period value S obtained by the period calculation unit 110, and obtains a common measurement time length value TSS for the illuminated measurement and the unilluminated measurement by multiplying the period value S by an integer, which is stored in advance in the measurement-time calculation unit 220. The obtained measurement time length value TSS is supplied to the timing controller 230. The timing controller 230 controls the timing of the illuminated measurement and the unilluminated measurement by outputting start control signals and stop control signals for the illuminated measurement and the unilluminated measurement to the spectrometer 50, the multichannel analyzer 140, and the shutter 30 based on the above measurement time length value TSS and a measurement time interval value TKK. The measurement time interval value TKK is stored in advance in the timing controller 230, and indicates a time interval between the end of the illuminated measurement and the start of the unilluminated measurement. The timing controller 230 further outputs timing control signals to the multichannel analyzer 140. The multichannel analyzer 140 receives from the spectrometer 50 intensity values indicating spectral distributions obtained by the illuminated measurement and the unilluminated measurement, based on the above timing control signals, and stores therein the received intensity values indicating spectral distributions. Further, the multichannel analyzer 140 subtracts the intensity values indicating the spectral distribution of the unilluminated measurement from the intensity values indicating the spectral distribution of the illuminated measurement, and supplies the subtraction result to the display device 150.

Details of the operations of measuring a spectrum of fluorescent light by the apparatus of the second embodiment are explained below.

First, the operations of setting the measurement time length value TSS in the optical measurement apparatus are explained.

Similar to the first embodiment, the mercury vapor lamp 21 is constantly emitting light, and the excitation light La passed through the band-pass filter 22 contains an emission line called as H line, having a center wavelength of 405 nm. Before the measurement of the spectral distribution, the shutter 30 is closed, and therefore the excitation light La is stopped by the shutter 30. The optical intensity measurement device 60 performs the measurement of the intensity of the light and supplies the measurement result to the controller 200, before the measurement of the spectral distribution.

In the same manner as with the first embodiment, the period calculation unit 110 calculates the period value S based on the intensity values of the background light supplied to the controller 200. Then, the period S is multiplied by the aforementioned integer stored in the measurement-time calculation unit 220 to obtain the measurement time length value TSS. In this example, the integer is two. Therefore, TSS=2S. The timing controller 230 stores the measurement time length value TSS as the measurement time length of each of the illuminated measurement and the unilluminated measurement. Thus, the set-up operation of the measurement time length value TSS is completed.

Next, details of the operations of the illuminated measurement and the unilluminated measurement in the second embodiment will be explained below.

Based on the above measurement time length value TSS and the measurement time interval value TKK between the end of the illuminated measurement and the start of the unilluminated measurement, the timing controller 230 outputs the start control signals and the stop control signals for the illuminated measurement and the unilluminated measurement to the spectrometer 50, the multichannel analyzer 140, and the shutter 30, as illustrated in FIG. 5. Thus, the illuminated measurement and the unilluminated measurement are performed in accordance with the start control signals and the stop control signals.

Referring to FIG. 5, when the illuminated measurement is started at time t1', the shutter 30 is opened, and the specimen 10 is illuminated by the excitation light La. In response to the illumination by the excitation light La, the specimen 10 emits fluorescent light. Also, at time t1', the spectrometer 50 starts the measurement. Thus, the fluorescent light KAA emitted by the specimen 10 and the background light HAA passed through the optical condenser system 40 are spectrally dispersed by the spectrally-dispersing portion 51, and the photometric portion 52 measures the intensities of the spectral components of the spectrally-dispersed light. At time t2', i.e., when time TSS has elapsed after time t1', the illuminated measurement is stopped. That is, at time t2', the spectrometer 50 stops the measurement, and holds the measured intensities of the spectral components. Also, the shutter 30 is closed to stop the illumination of the specimen 10 by the excitation light La. The above intensities obtained by the illuminated measurement, which indicate a sum of spectra of the background light HAA and the fluorescent light KAA, are supplied to and stored in the multichannel analyzer 140 at time t3'.

At time t4', i.e., when time TKK has elapsed after time t2', the unilluminated measurement is started. That is, the spectrometer 50 starts the measurement of the intensities of the spectral components of the spectrally dispersed light. During the unilluminated measurement, the shutter 30 is closed. Since the specimen 10 is not illuminated by the excitation light La, the intensities KBB of the fluorescent light are zero, and the spectrometer 50 measures the intensities of the background light HBB only. At time t5', i.e., when time TSS has elapsed after time t4', the unilluminated measurement is stopped. That is, at time t5', the spectrometer 50 stops the measurement, and holds the measured intensities of the spectral components. The intensities obtained by the unilluminated measurement, i.e., the intensities of the background light HBB, are supplied to and stored in the multichannel analyzer 140 at time t6'.

Next, the operations of calculation and display of the spectral distributions in the second embodiment will be explained below.

Similar to the first embodiment, the multichannel analyzer 140 subtracts the intensity values indicating the spectral distribution HBB of the unilluminated measurement from the intensity values indicating the spectral distribution of the illuminated measurement to obtain the spectral distribution of the fluorescent light KAA, and supplies the calculation result to the display device 150.

Although the illuminated measurement and the illuminated measurement are performed at different times, the lengths of the measurement times of the illuminated measurement and the unilluminated measurement are the same, and the identical length of measurement time equals an integer multiple of the period of the variation of the intensity of the background light. Therefore, the contribution HAA of the background light in the spectral distribution of the illuminated measurement illustrated in FIG. 5 is considered to be substantially identical to the spectral distribution HBB of the unilluminated measurement illustrated in FIG. 5. Therefore, the spectral distribution KAA of the fluorescent light included in the illuminated measurement can be obtained by subtracting the spectral distribution HBB obtained by the unilluminated measurement from the spectral distribution obtained by the illuminated measurement.

The spectral distribution KAA of the fluorescent light obtained as above is then displayed as an image by the display device 150.

As described above, by using the optical measurement apparatus of the second embodiment of the present invention, a spectrum of the light to be measured can be measured with high accuracy even when the wavelength range of the background light overlaps the wavelength range of the light to be measured, which has been emitted from a specimen in response to illumination of the specimen, or has been reflected by or has penetrated through a specimen when the specimen is illuminated.

Variations of First and Second Embodiments

In addition to the above constructions of the first and second embodiments of the present invention, it is possible to construct various variations and modifications within the scope of the present invention. The following are examples of such variations and modifications.

(1) As illustrated in FIG. 2 or 5, in each of the first and second embodiments, the background light is a sum of the constant component e (illustrated in FIG. 2 or 5) and the cyclically varying component f (illustrated in FIG. 2 or 5). However, the spectral distribution of the fluorescent light can also be obtained in the same manner as the above cases even when the background light contains only the constant component e, or when the background light contains only the cyclically varying component f.

(2) In the illuminated measurement in the first and second embodiments, the time for which the specimen 10 is actually illuminated by the excitation light La, i.e., the time for which the shutter 30 is actually open, may be different from the length TS or TSS of the measurement time. For example, the specimen 10 may be illuminated by the excitation light La in a pulselike manner, or the intensity of the excitation light La may be varied during the measurement.

(3) Although the illuminated measurement is performed first in the examples of FIGS. 2 and 5, instead, the unilluminated measurement may be performed first.

(4) When the period of the variation of the intensity of the background light is known in advance of the measurement of the spectral distribution, the measurement of the period by the period calculation unit 110 is unnecessary. In this case, the known value of the period may be stored in advance in the period calculation unit 110 or the measurement-timing-difference calculation unit 120 or the measurement-time calculation unit 220.

(5) In the first embodiment, the integer stored in the measurement-timing-difference calculation unit 120 may be any integer, instead of two.

(6) In the second embodiment, the integer stored in the measurement-time calculation unit 220 may be any integer, instead of two.

(7) Although it is unnecessary to perform each of the illuminated measurement and the unilluminated measurement in synchronization with the cyclic variation of the background light, each of the illuminated measurement and the unilluminated measurement may be performed in synchronization with the cyclic variation of the background light.

(8) Although the first to fourth aspects of the present invention are applied to the measurement of a spectrum of fluorescent light in the first and second embodiments, the first to fourth aspects of the present invention can also be applied to the measurement of a spectrum of phosphorescent light emitted from the specimen 10 or Raman scattering light scattered by the specimen 10, or a spectrum of light which is polarized, absorbed, or attenuated when light incident on the specimen 10 is reflected by the specimen, by modifying the characteristic of the pass filter in the optical condenser system 40, the wavelength characteristics of the lamp and the band-pass filter in the light source 20, the length of the measurement times in the illuminated measurement and the unilluminated measurement, and the difference between the timings of the illuminated measurement and the unilluminated measurement.

(9) When the light source 20 and the shutter 30 are placed on the opposite side of the optical condenser system 40 with respect to the specimen 10, the optical condenser system 40 can collect light which has been emitted from the light source 20 and light which has been penetrated through the specimen 10. That is, when the apparatuses of FIGS. 1 and 4 are modified like this, a spectrum of light which has been polarized, absorbed, or attenuated by the penetration through the specimen 10 can be measured by the apparatuses of FIGS. 1 and 4, in addition to the fluorescent light or phosphorescent light emitted from the specimen 10 or the Raman scattering light scattered by the specimen 10 as mentioned above.

(10) When the optical condenser system 40 is replaced with an image-forming optical system, the spectrometer 50 is replaced with an imaging unit, the spectral-dispersing portion 51 and the photometric portion 52 are replaced with an imaging device (e.g., a device using a charge-coupled device (CCD)) and an imaging driver, and the multichannel analyzer 140 is replaced with an image processing unit, an image of an intensity distribution of light to be measured, emitted from the surface of the specimen, may be formed on the imaging device by using the image-forming optical system, where the light to be measured may be fluorescent light or phosphorescent light emitted from the specimen, or the Raman scattering light scattered by the specimen, or light which has been polarized, absorbed, or attenuated by the specimen. The light intensities of respective pixels of the above image on the imaging device can be converted into image signals by the imaging driver, and the image signals may be output to and stored in the image processing unit. In this case, the aforementioned timing controller can control timing of the above operation of the imaging unit by outputting control signals, so that the illuminated measurement and the unilluminated measurement can be performed in the same manner as either of the first and second embodiments, and true intensities of the light to be measured, which do not include the background light, can be obtained by the image processing unit as an image (two-dimensional image) by subtracting image signals obtained by the unilluminated measurement from image signals obtained by the illuminated measurement.

Common Construction of Third to Seventh Embodiments

FIG. 6 is a diagram illustrating an outline of a construction of an apparatus for measuring a spectrum of fluorescent light, which can be commonly used in the third, fourth, fifth, sixth, and seventh embodiments of the present invention. In the construction of FIG. 6, the methods according to the third, fifth, and seventh aspects of the present invention can be executed, and therefore the construction of FIG. 6 can realize the image processing apparatuses according to the sixth, eighth, and tenth aspects of the present invention, as explained below.

Figure 7:
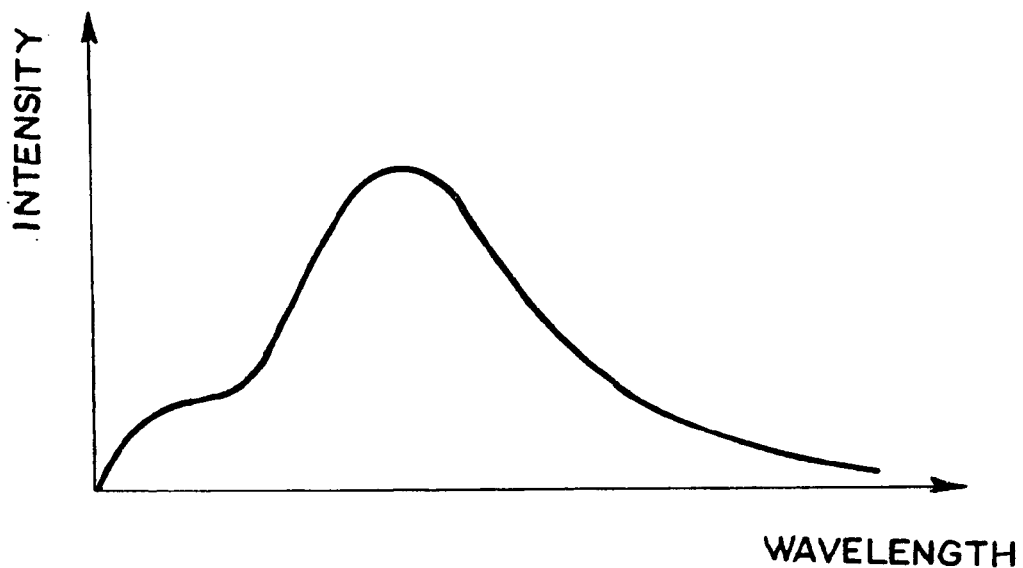
FIG. 7 is a diagram illustrating an example of a spectral distribution.

The optical measurement apparatus of FIG. 6 contains a light source 320, a measurement unit 330, a control unit 400, and an display unit 350. The light source 320 emits excitation light Le for illuminating a specimen 310, where the excitation light Le has wavelengths in the vicinity of 410 nm. The measurement unit 330 detects a spectral distribution of light, and outputs values of the detected spectral distribution, where the detected light includes fluorescent light Ke which is emitted from the specimen 310 in response to the illumination of the excitation light Le. The spectral distribution of light is a distribution of intensities of spectral components of light, for example, as illustrated in FIG. 7. The control unit 400 controls timing of the measurement based on periods of intensity variations of background light which is included in and should be eliminated from the detected spectral distribution, and data of the periods of intensity variations of background light are input from outside. In addition, the control unit 400 eliminates, by calculation, influence of the background light from the values of the spectral distribution output from the measurement unit 330, and outputs a result of the calculation. The display unit 350 displays the result of the calculation output from the 400.

In the measurement unit 330, an excitation-light cut filter 333 is provided, and an optical system 332 and a spectrophotometer 331 are arranged along the optical axis of the measurement unit 330. The optical system 332 condenses the fluorescent light Ke emitted from the specimen 310, and the spectrophotometer 331 detects the spectral distribution of the fluorescent light Ke condensed by the optical system 332, by spectrophotometry, and supplies the detected spectral distribution to the control unit 400.

The control unit 400 contains a measurement condition setting unit 420, a timing controller 430, and a calculation processing unit 440. The measurement condition setting unit 420 sets a measurement condition based on the data of the periods of intensity variations of background light which are input from outside. In particular, the measurement condition setting unit 420 sets in the timing controller 430 a condition on the measurement timing. The timing controller 430 generates control signals for starting and stopping the illumination of the excitation light Le and other control signals for starting and stopping the operation of the spectrophotometer 331, based on the measurement condition set by the measurement condition setting unit 420, and outputs the control signals to the light source 320 and the spectrophotometer 331. The calculation processing unit 440 processes the values of the spectral distribution supplied from the spectrophotometer 331 by calculation, and outputs the result of the processing to the display unit 350.

The operations of the apparatus of FIG. 6 are explained below.

First, the data Da of the periods of the intensity variation of the background light which is to be eliminated are input from outside through the connector 410 to the measurement condition setting unit 420. In this example, the data Da include the periods of intensity variations of two types of background light, respectively caused by room illumination, and other illumination which is provided for observing the specimen 310. The values of the periods are obtained in advance by measurement, for example, by using another measurement apparatus. The measurement condition setting unit 420 determines values of durations of measurement, a time difference between the illuminated measurement and the unilluminated measurement, and a duration of the illumination of the excitation light Le based on the data Da of the periods, obtains timing of the illumination of the excitation light Le, the illuminated measurement, and the unilluminated measurement based on the determined values, and supplies information on the obtained timing to the timing controller 430. The specimen 310 is illuminated by the excitation light Le in the illuminated measurement, and the specimen 310 is not illuminated by the excitation light Le in the unilluminated measurement.

When the timing controller 430 receives information on the timing of the illumination of the excitation light Le, the illuminated measurement, and the unilluminated measurement, the timing controller 430 outputs to the light source 320 and the measurement unit 330 the control signals for starting and stopping the illumination of the excitation light Le and starting and stopping the operation of the spectrophotometer 331. Thus, the illuminated measurement and the unilluminated measurement can be performed.

When the illuminated measurement is performed, the fluorescent light Ke emitted by the illumination of the excitation light Le and the aforementioned two types of background light enter the spectrophotometer 331, and the spectrophotometer 331 detects the fluorescent light Ke and the two types of background light as a spectral distribution in the illuminated measurement. When the unilluminated measurement is performed, the fluorescent light Ke is not emitted from the specimen 310, and only the aforementioned two types of background light enter the spectrophotometer 331. Therefore, the spectrophotometer 331 detects only the two types of background light as a spectral distribution in the unilluminated measurement. The above spectral distributions in the illuminated measurement and the unilluminated measurement are supplied to the calculation processing unit 440, and the influence of the background light is eliminated from the spectral distribution in the illuminated measurement by calculation.

Operations of Third Embodiment

Figure 8:
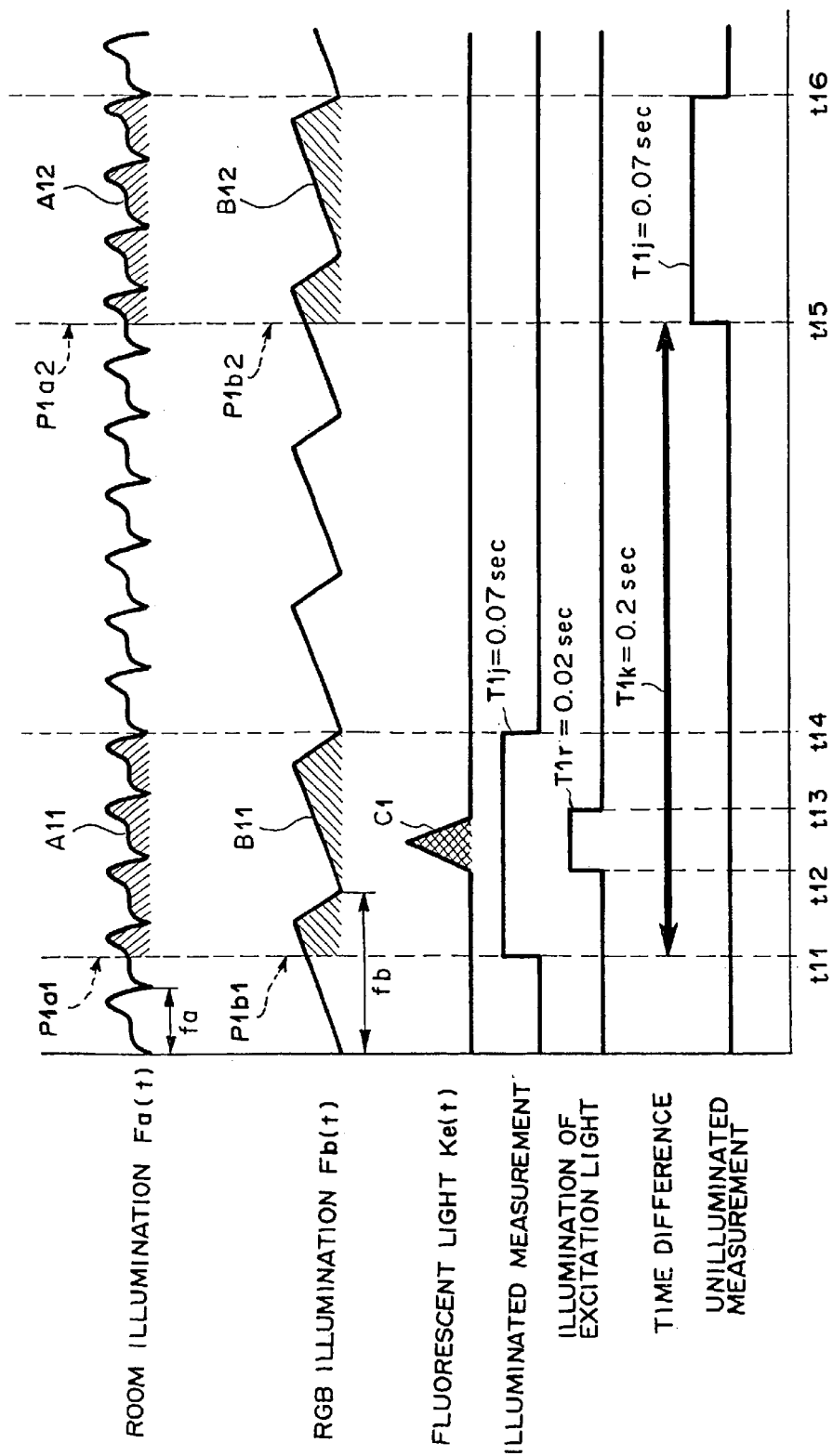
FIG. 8 is a timing chart of the operations in the third embodiment, which realizes the fifth and fourth aspects of the present invention.

FIG. 8 is a timing chart of the operations in the third embodiment, which realizes the fifth and sixth aspects of the present invention. In the example of FIG. 8, it is assumed that the above-mentioned two types of background light is room illumination Fa(t) and RGB illumination Fb(t). The period fa of the intensity variation of the room illumination Fa(t) is 0.02 sec (i.e., the frequency is 50 Hz). The RGB illumination Fb(t) includes red, green, and blue illumination for a field sequential image pick up system, and the period fb of the intensity variation of the RGB illumination Fb(t) is 0.05 sec (i.e., the frequency is 20 Hz).

When data Da of the above periods fa and fb of the intensity variations of the room illumination Fa(t) and the RGB illumination Fb(t) are supplied to the measurement condition setting unit 420, the measurement condition setting unit 420 determines values of durations of illuminated measurement and unilluminated measurement, a time difference between the illuminated measurement and the unilluminated measurement, and a duration of the illumination of the excitation light Le based on the data Da of the periods fa and fb, and obtains timing of the illumination of the excitation light Le, the illuminated measurement, and the unilluminated measurement based on the determined values.

According to the fifth or sixth aspects of the present invention, the time difference T1$k$ between the illuminated measurement and the unilluminated measurement is set to be an integer multiple of the least common multiple of the above periods fa and fb of the intensity variations of the room illumination Fa(t) and the RGB illumination Fb(t). In this example, the time difference T1$k$ is determined to be 0.2 sec, which is twice the least common multiple (0.1 sec) of fa=0.02 sec and fb=0.05 sec. In addition, the duration T1$j$ of each of the illuminated measurement and the unilluminated measurement is determined to be 0.07 sec, which is shorter than the above time difference T1$k$. The duration T1$r$ of the illumination of the excitation light Le is determined to be 0.02 sec, which is shorter than the duration T1$j$ of the illuminated measurement.

Based on the above values of the time difference T1$k$ and the durations T1$j$ and T1$r$, timing t11, t14 of the illuminated measurement, timing t12, t13 of the illumination of the excitation light Le, and timing t15, t16 of the unilluminated measurement are obtained. The information on the timing t11 to t16 is supplied from the measurement condition setting unit 420 to the timing controller 430, and is then converted into the aforementioned control signals for controlling the light source 320 and the measurement unit 330. When the control signals are supplied to the light source 320 and the measurement unit 330, the following operations are performed.

When the illuminated measurement is commenced at time t11, the spectrophotometer 331 detects a spectrum of light which enters the spectrophotometer 331 through the optical system 332, as a spectral distribution SP1$c$ in the illuminated measurement. While the illuminated measurement is performed for the duration T1$j$ of 0.07 sec continuing from time t11 to time t14, the specimen 310 is illuminated with the excitation light Le for the duration T1$r$ of 0.02 sec continuing from time t12 to time t13. In response to the illumination of the excitation light Le, the fluorescent light Ke is emitted from the specimen 310. The fluorescent light Ke enters the spectrophotometer 331, and is detected by the spectrophotometer 331. Although the excitation light Le is reflected by the specimen 310, the reflected excitation light Le is shut off by the excitation-light cut filter 333 so that the reflected excitation light Le is not detected by spectrophotometer 331.

After the illuminated measurement is completed at time t14, the unilluminated measurement is commenced at time t15, which is 0.2 sec (the time difference T1$k$) after time t11. In the unilluminated measurement, the spectrophotometer 331 detects a spectrum of light which enters the spectrophotometer 331 through the optical system 332, to obtain a spectral distribution SP1$s$ in the unilluminated measurement. While the unilluminated measurement is performed for the duration T1$j$ of 0.07 sec continuing from time t15 to time t16, the specimen 310 is not illuminated with the excitation light Le. Therefore, no fluorescent light Ke is detected by the spectrophotometer 331 in the unilluminated measurement.

Next, the values of the spectral distribution SP1$c$ in the illuminated measurement and the spectral distribution SP1$s$ in the unilluminated measurement are transferred from the spectrophotometer 331 to the calculation processing unit 440. The calculation processing unit 440 subtracts the values of the spectral distribution SP1$s$ in the unilluminated measurement from the values of the spectral distribution SP1$c$ in the illuminated measurement, to obtain a spectral distribution SP1$k$ which includes a true spectral distribution of the fluorescent light Ke and does not include influence of the background light, and the spectral distribution SP1$k$ is displayed by the display unit 350.

Details of the operation of obtaining the true spectral distribution SP1$k$ of the fluorescent light Ke are as follows.

Since the time difference T1$k$ between the illuminated measurement and the unilluminated measurement is equal to twice the least common multiple of the above periods fa and fb of the intensity variations of the room illumination Fa(t) and the RGB illumination Fb(t), the time difference T1$k$ is ten times the period fa, and is also four times the period fb. Therefore, the phase P1$a$1 of the cyclic variation of the room illumination Fa(t) at time t11 at which the illuminated measurement is commenced is identical with the phase P1$a$2 of the cyclic variation of the room illumination Fa(t) at time t15 at which the unilluminated measurement is commenced, and the phase P1$b$1 of the cyclic variation of the RGB illumination Fb(t) at time t11 at which the illuminated measurement is commenced is identical with the phase P1$b$2 of the cyclic variation of the RGB illumination Fb(t) at time t15 at which the unilluminated measurement is commenced. In addition, the durations T1$j$ (=0.07 sec) of the illuminated measurement and the unilluminated measurement are identical.

Therefore, the quantity A11 of the room illumination Fa(t) detected in the illuminated measurement and the quantity A12 of the room illumination Fa(t) detected in the unilluminated measurement are identical, and the quantity B11 of the RGB illumination Fb(t) detected in the illuminated measurement and the quantity B12 of the RGB illumination Fb(t) detected in the unilluminated measurement are also identical. Further, a spectral distribution SP1$a$1 of the room illumination Fa(t) detected in the illuminated measurement and a spectral distribution SP1$a$2 of the room illumination Fa(t) detected in the unilluminated measurement are identical, and a spectral distribution SP1$b$1 of the RGB illumination Fb(t) detected in the illuminated measurement and a spectral distribution SP1$b$2 of the RGB illumination Fb(t) detected in the unilluminated measurement are also identical.

On the other hand, the specimen 310 is illuminated with the excitation light Le for the duration T1$r$ of 0.02 sec during the illuminated measurement, and the fluorescent light Ke is emitted from the specimen 310 in response to the illumination of the excitation light Le. Therefore, a quantity C1 of the fluorescent light Ke having a spectral distribution SP1$k$ is desired to be detected by the spectrophotometer 331. However, due to the existence of the background light, the spectral distribution SP1$c$ actually detected by the spectrophotometer 331 in the illuminated measurement is a sum of the spectral distribution SP1$k$ of the fluorescent light Ke, the above-mentioned spectral distribution SP1$a$1 of the room illumination Fa(t), and the spectral distribution SP1$b$1 of the RGB illumination Fb(t).

Therefore, the aforementioned spectral distribution SP1$k$, which is a true spectral distribution of the fluorescent light Ke and does not include the above spectral distribution SP1$a$1 of the room illumination Fa(t) and the spectral distribution SP1$b$1 of the RGB illumination Fb(t), can be obtained by subtracting the spectral distribution SP1$a$2 of the room illumination Fa(t) and the spectral distribution SP1$b$2 of the RGB illumination Fb(t) from the spectral distribution SP1$c$ which is actually detected by the spectrophotometer 331 in the illuminated measurement. That is, since SP1$a$1=SP1$a$2, and SP1$b$1=SP1$b$2, $$SP1k=(SP1k+SP1a1+SP1b1)-(SP1a2+SP1b2)=SP1c-SP1s.$$

The result of this calculation is displayed by the display unit 350.

Operations of Fourth Embodiment

Figure 9:
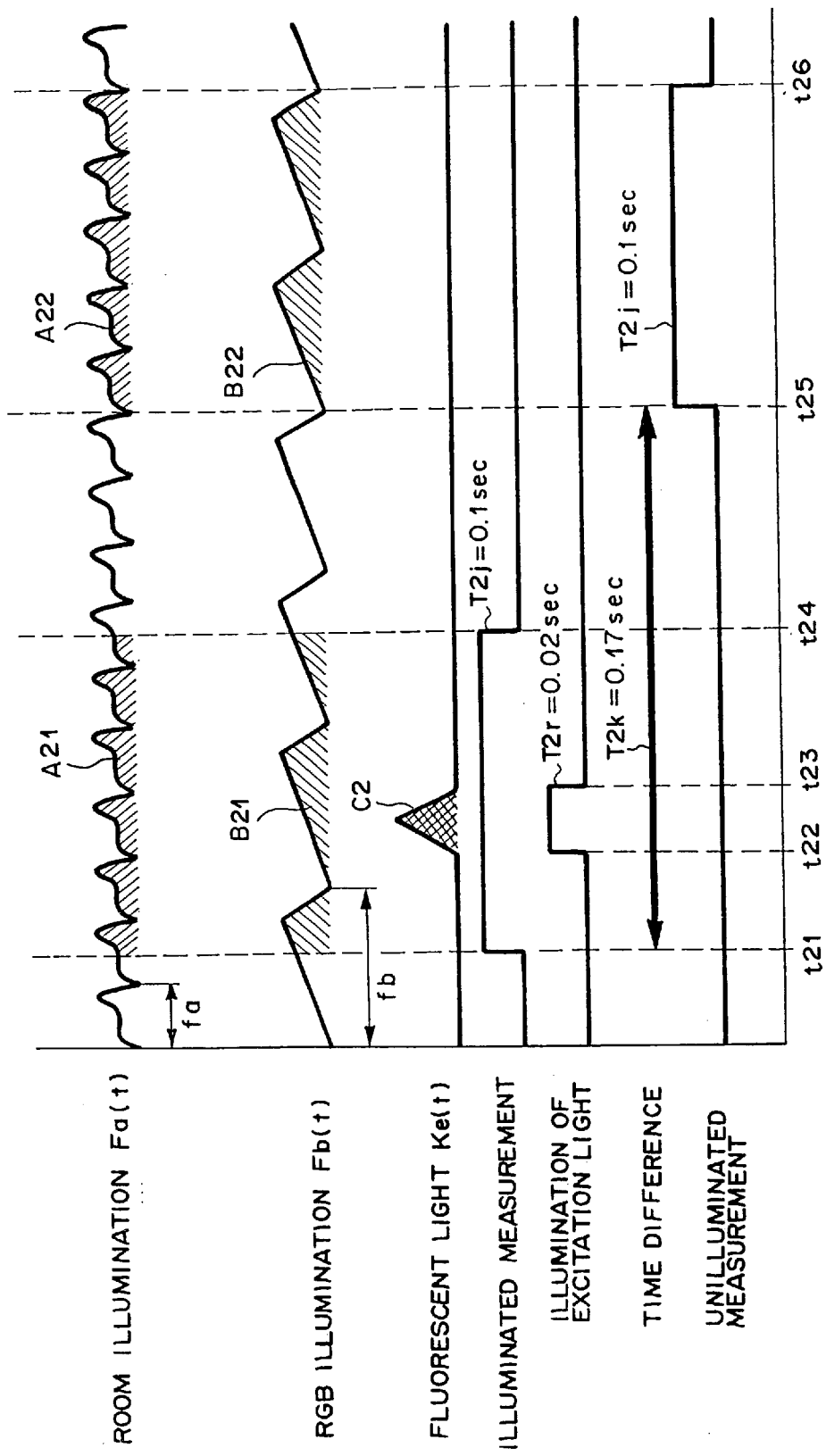
FIG. 9 is a timing chart of the operations in the fourth embodiment, which realizes the seventh and eighth aspects of the present invention.

FIG. 9 is a timing chart of the operations in the fourth embodiment, which realizes the seventh and eighth aspects of the present invention. In the example of FIG. 9, it is also assumed that the room illumination Fa(t) having the period fa(=0.02 sec) and the RGB illumination Fb(t) having the period fb(=0.05 sec) exist as the two types of background light, where the periods fa and fb are periods of the intensity variations of the room illumination Fa(t) and the RGB illumination Fb(t), respectively.

Similar to the third embodiment, the measurement condition setting unit 420 determines values of durations of illuminated measurement and unilluminated measurement, a time difference between the illuminated measurement and the unilluminated measurement, and a duration of the illumination of the excitation light Le based on the data Da of the periods fa and fb, and obtains timing of the illumination of the excitation light Le, the illuminated measurement, and the unilluminated measurement based on the determined values.

According to the seventh or eighth aspects of the present invention, the duration T2$j$ of each of the illuminated measurement and the unilluminated measurement is set to be an integer multiple of the least common multiple of the above periods fa and fb. In this example, the duration T2$j$ of each of the illuminated measurement and the unilluminated measurement is determined to be 0.1 sec, which is identical with the least common multiple (0.1 sec) of fa=0.02 sec and fb=0.05 sec. In addition, the time difference T2$k$ between the illuminated measurement and the unilluminated measurement is determined to be 0.17 sec, which is longer than the above duration T2$j$, and the duration T2$r$ of the illumination of the excitation light Le is determined to be 0.02 sec, which is shorter than the duration T2$j$ of the illuminated measurement.

Based on the above values of the time difference T2$k$ and the durations T2$j$ and T2$r$, timing t21, t24 of the illuminated measurement, timing t22, t23 of the illumination of the excitation light Le, and timing t25, t26 of the unilluminated measurement are obtained. The information on the timing t21 to t26 is supplied from the measurement condition setting unit 420 to the timing controller 430, and is then converted into the aforementioned control signals for controlling the light source 320 and the measurement unit 330. When the control signals are supplied to the light source 320 and the measurement unit 330, the following operations are performed.

When the illuminated measurement is commenced at time t21, the spectrophotometer 331 detects a spectrum of light which enters the spectrophotometer 331 through the optical system 332, as a spectral distribution SP2$c$ in the illuminated measurement. While the illuminated measurement is performed for the duration T2$j$ of 0.1 sec continuing from time t21 to time t24, the specimen 310 is illuminated with the excitation light Le for the duration T2$r$ of 0.02 sec continuing from time t22 to time t23. In response to the illumination of the excitation light Le, the fluorescent light Ke is emitted from the specimen 310. The fluorescent light Ke enters the spectrophotometer 331, and is detected by the spectrophotometer 331.

The illuminated measurement is completed at time t24. Then, at time t25, which is 0.07 sec (the time difference T2$k$) after time t21, the unilluminated measurement is commenced. In the unilluminated measurement, the spectrophotometer 331 detects a spectrum of light which enters the spectrophotometer 331 through the optical system 332, as a spectral distribution SP2$s$ in the unilluminated measurement. While the unilluminated measurement is performed for the duration T2$j$ of 0.1 sec continuing from time t25 to time t26, the specimen 310 is not illuminated with the excitation light Le. Therefore, no fluorescent light Ke is detected by the spectrophotometer 331 in the unilluminated measurement.

Next, the values of the spectral distribution SP2c in the illuminated measurement and the spectral distribution SP2s in the unilluminated measurement are transferred from the spectrophotometer 331 to the calculation processing unit 440. The calculation processing unit 440 subtracts the values of the spectral distribution SP2s in the unilluminated measurement from the values of the spectral distribution SP2c in the illuminated measurement to obtain a spectral distribution SP2k, which shows a true spectral distribution of the fluorescent light Ke and does not include influence of the background light. Then, the spectral distribution SP2k is displayed by the display unit 350.

Details of the operation of obtaining the true spectral distribution SP2k of the fluorescent light Ke are as follows.

Since the duration T2j of each of the illuminated measurement and the unilluminated measurement is equal to the least common multiple of the above periods fa and fb, the duration T2j is five times the period fa, and is also twice the period fb. Therefore, regardless of the phases of the background light at the beginning times of the illuminated measurement and the unilluminated measurement, in each of the illuminated measurement and the unilluminated measurement, measurement of light is concurrently performed for five periods of the cyclic variation of the room illumination Fa(t) and for two periods of the cyclic variation of the RGB illumination Fb(t). That is, the quantity A21 of the room illumination Fa(t) detected in the illuminated measurement is identical with the quantity A22 of the room illumination Fa(t) detected in the unilluminated measurement, and the spectral distribution SP2a1 of the room illumination Fa(t) detected in the illuminated measurement is identical with the spectral distribution SP2a2 of the room illumination Fa(t) detected in the unilluminated measurement. In addition, the quantity of light B21 of the RGB illumination Fb(t) detected in the illuminated measurement is identical with the quantity of light B22 of the RGB illumination Fb(t) detected in the unilluminated measurement, and the spectral distribution SP2b1 of the RGB illumination Fb(t) detected in the illuminated measurement is identical with the spectral distribution SP2b2 of the RGB illumination Fb(t) detected in the unilluminated measurement.

On the other hand, the specimen 310 is illuminated with the excitation light Le for the duration T2r of 0.02 sec during the illuminated measurement, and the fluorescent light Ke is emitted from the specimen 310 in response to the illumination of the excitation light Le. Therefore, a quantity C2 of the fluorescent light Ke having the spectral distribution SP2k is desired to be detected by the spectrophotometer 331. However, due to the existence of the background light, the spectral distribution SP2c actually detected by the spectrophotometer 331 in the illuminated measurement is a sum of the spectral distribution SP2k of the fluorescent light Ke, the above-mentioned spectral distribution SP2a1 of the room illumination Fa(t), and the spectral distribution SP2b1 of the RGB illumination Fb(t).

Therefore, the aforementioned spectral distribution SP2k, which shows a true spectral distribution of the fluorescent light Ke and does not include the above spectral distribution SP2a1 of the room illumination Fa(t) and the spectral distribution SP2b1 of the RGB illumination Fb(t), can be obtained by subtracting the spectral distribution SP2a2 of the room illumination Fa(t) and the spectral distribution SP2b2 of the RGB illumination Fb(t) from the spectral distribution SP2c which is actually detected by the spectrophotometer 331 in the illuminated measurement. That is, since SP2a1=SP2a2, and SP2b1=SP2b2, $$SP2k = (SP2k + SP2a1 + SP2b1) - (SP2a2 + SP2b2) = SP2c - SP2s.$$

The result of this calculation is displayed by the display unit 350.

Operations of Fifth Embodiment

Figure 10:
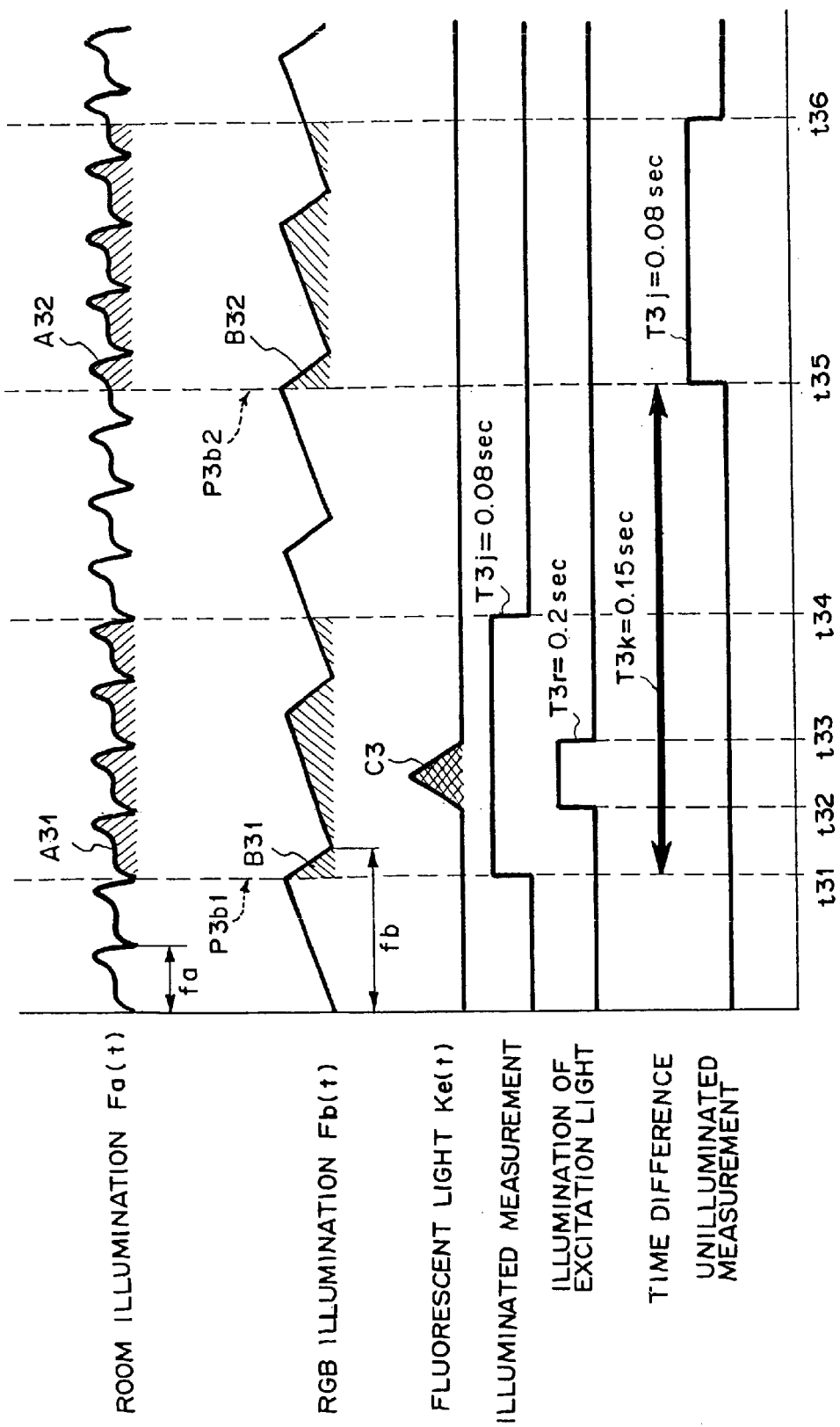
FIG. 10 is a timing chart of the operations in the fifth embodiment, which realizes the ninth and tenth aspects of the present invention.

FIG. 10 is a timing chart of the operations in the fifth embodiment, which realizes the ninth and tenth aspects of the present invention. In the example of FIG. 10, it is also assumed that the room illumination Fa(t) having the period fa(=0.02 sec) and the RGB illumination Fb(t) having the period fb(=0.05 sec) exist as the two types of background light, where the periods fa and fb are periods of the intensity variations of the room illumination Fa(t) and the RGB illumination Fb(t), respectively.

Similar to the third and fourth embodiments, the measurement condition setting unit 420 determines values of durations of illuminated measurement and unilluminated measurement, a time difference between the illuminated measurement and the unilluminated measurement, and a duration of the illumination of the excitation light Le based on the data Da of the periods fa and fb, and obtains timing of the illumination of the excitation light Le, the illuminated measurement, and the unilluminated measurement based on the determined values.

According to the ninth or tenth aspects of the present invention, the illuminated measurement and the unilluminated measurement are performed for the same duration T3j, and the duration T3j is equal to an integer multiple of one of the periods fa and fb, and the time difference T3k between the beginning times of the illuminated measurement and the unilluminated measurement is an integer multiple of the other of the periods fa and fb. In this example, the time difference T3k between the illuminated measurement and the unilluminated measurement is determined to be 0.15 sec, which is three times the period fb, and the duration T3j of each of the illuminated measurement and the unilluminated measurement is determined to be 0.08 sec, which is four times the period fa. In addition, the duration T3r of the illumination of the excitation light Le is determined to be 0.02 sec, which is shorter than the duration T3j of the illuminated measurement.

Based on the above values of the time difference T3k and the durations T3j and T3r, timing t31, t34 of the illuminated measurement, timing t32, t33 of the illumination of the excitation light Le, and timing t35, t36 of the unilluminated measurement are obtained. The information on the timing t31 to t36 is supplied from the measurement condition setting unit 420 to the timing controller 430, and is then converted into the aforementioned control signals for controlling the light source 320 and the measurement unit 330. When the control signals are supplied to the light source 320 and the measurement unit 330, the following operations are performed.

When the illuminated measurement is commenced at time t31, the spectrophotometer 331 detects a spectrum of light which enters the spectrophotometer 331 through the optical system 332, as a spectral distribution SP2c in the illuminated measurement. While the illuminated measurement is performed for the duration T3j of 0.1 sec continuing from time t31 to time t34, the specimen 310 is illuminated with the excitation light Le for the duration T3r of 0.02 sec continuing from time t32 to time t33. In response to the illumination of the excitation light Le, the fluorescent light Ke is emitted from the specimen 310. The fluorescent light Ke enters the spectrophotometer 331, and is detected by the spectrophotometer 331.

The illuminated measurement is completed at time t34. Then, at time t35, which is 0.15 sec (the time difference T3k) after time t31, the unilluminated measurement is commenced. In the unilluminated measurement, the spectrophotometer 331 detects a spectrum of light which enters the spectrophotometer 331 through the optical system 332, as a spectral distribution SP3s in the unilluminated measurement. While the unilluminated measurement is performed for the duration T3j of 0.08 sec continuing from time t35 to time t36, the specimen 310 is not illuminated with the excitation light Le. Therefore, no fluorescent light Ke is detected by the spectrophotometer 331 in the unilluminated measurement.

Next, the values of the spectral distribution SP3c in the illuminated measurement and the spectral distribution SP3s in the unilluminated measurement are transferred from the spectrophotometer 331 to the calculation processing unit 440. The calculation processing unit 440 subtracts the values of the spectral distribution SP3s in the unilluminated measurement from the values of the spectral distribution SP3c in the illuminated measurement to obtain a spectral distribution SP3k, which shows a true spectral distribution of the fluorescent light Ke and does not include influence of the background light. Then, the spectral distribution SP3k is displayed by the display unit 350.

Details of the operation of obtaining the true spectral distribution SP3k of the fluorescent light Ke are as follows.

The duration T3j of each of the illuminated measurement and the unilluminated measurement is four times the above period fa of the intensity variations of the room illumination Fa(t). Therefore, regardless of the phases of the room illumination Fa(t) at the beginning times of the illuminated measurement and the unilluminated measurement, measurement of light is performed for four periods of the cyclic variation of the room illumination Fa(t) in each of the illuminated measurement and the unilluminated measurement. That is, the quantity A31 of the room illumination Fa(t) detected in the illuminated measurement is identical with the quantity A32 of the room illumination Fa(t) detected in the unilluminated measurement, and the spectral distribution SP3a1 of the room illumination Fa(t) detected in the illuminated measurement is identical with the spectral distribution SP3a2 of the room illumination Fa(t) detected in the unilluminated measurement.

In addition, since the time difference T3k between the illuminated measurement and the unilluminated measurement is three times the period fb of the RGB illumination Fb(t), the phase P3b1 of the RGB illumination Fb(t) at time t31 at which the illuminated measurement is commenced is identical with the phase P3b2 of the RGB illumination Fb(t) at time t35 at which the unilluminated measurement is commenced. Further, the durations T3j (=0.08 sec) of the illuminated measurement and the unilluminated measurement are identical. Therefore, the quantity B31 of the RGB illumination Fb(t) detected in the illuminated measurement and the quantity B32 of the RGB illumination Fb(t) detected in the unilluminated measurement are identical, and the spectral distribution SP3b1 of the RGB illumination Fb(t) detected in the illuminated measurement and the spectral distribution SP3b2 of the RGB illumination Fb(t) detected in the unilluminated measurement are also identical.

On the other hand, the specimen 310 is illuminated with the excitation light Le for the duration T3r of 0.02 sec during the illuminated measurement, and fluorescent light Ke is emitted from the specimen 310 in response to the illumination of the excitation light Le. Therefore, a quantity C3 of the fluorescent light Ke having a spectral distribution SP3k is desired to be detected by the spectrophotometer 331. However, due to the existence of the background light, a spectral distribution SP3c actually detected by the spectrophotometer 331 in the illuminated measurement is a sum of the spectral distribution of the fluorescent light Ke, the above-mentioned spectral distribution SP3a1 of the room illumination Fa(t) and the spectral distribution SP3b1 of the RGB illumination Fb(t).

Therefore, the aforementioned spectral distribution SP3k, which shows a true spectral distribution of the fluorescent light Ke and does not include the above spectral distribution SP3a1 of the room illumination Fa(t) and the spectral distribution SP3b1 of the RGB illumination Fb(t), can be obtained by subtracting the spectral distribution SP3a2 of the room illumination Fa(t) and the spectral distribution SP3b2 of the RGB illumination Fb(t) from the spectral distribution SP3c actually detected by the spectrophotometer 331 in the illuminated measurement. That is, since SP3a1=SP3a2, and SP3b1=SP3b2, $$SP3k=(SP3k+SP3a1+SP3b1)-(SP3a2+SP3b2)=SP3c-SP3s.$$

The result of this calculation is displayed by the display unit 350.

Operations of Sixth Embodiment

Figure 11:
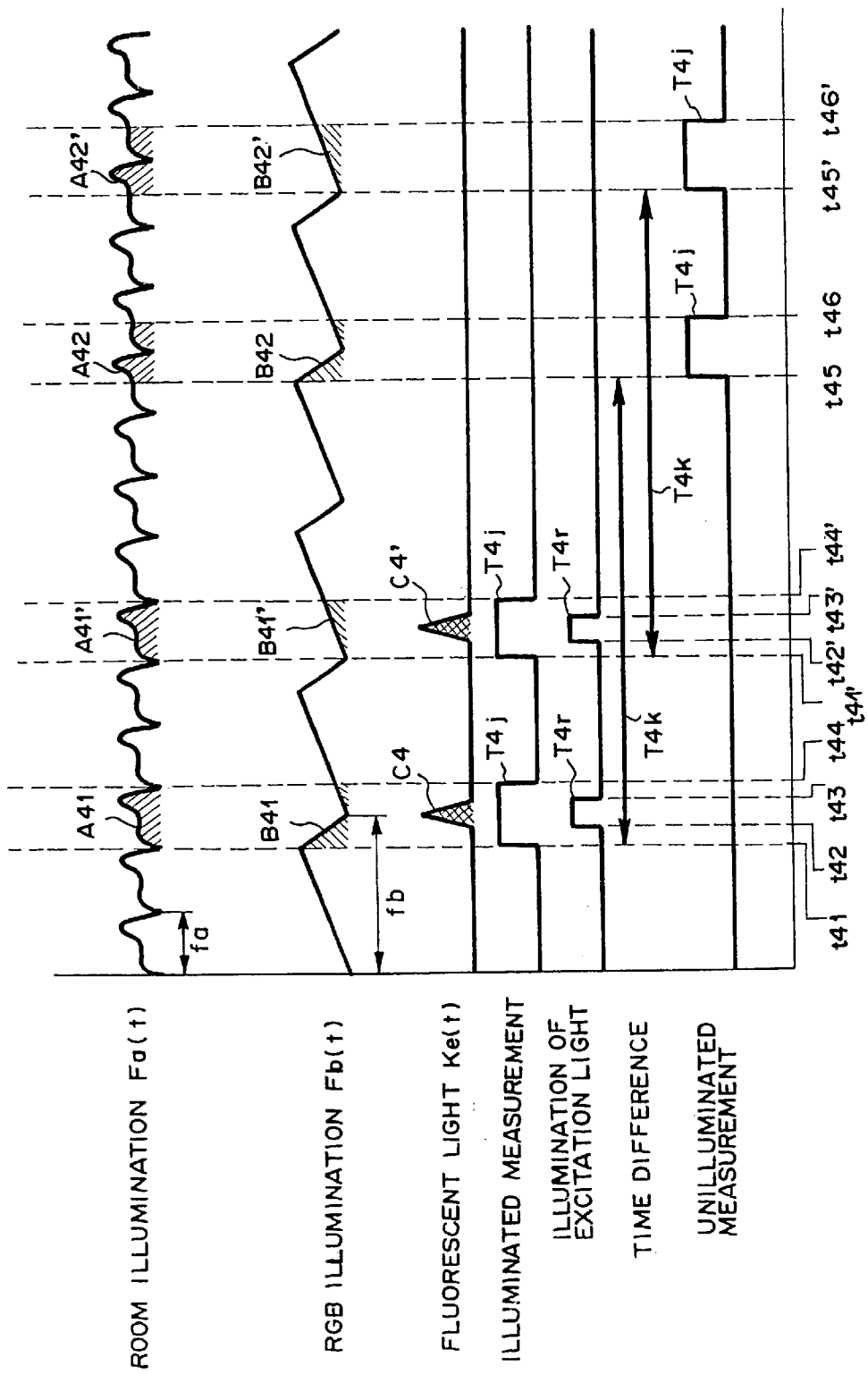
FIG. 11 is a timing chart of the operations in the sixth embodiment, which realizes the ninth and tenth aspects of the present invention.

FIG. 11 is a timing chart of the operations in the sixth embodiment, which realizes the ninth and tenth aspects of the present invention. In the sixth embodiment, two sets of illuminated measurement and unilluminated measurement are performed, and the operations in each set are similar to the operations in the fifth embodiment.

In the example of FIG. 11, it is also assumed that the same types of background light as the third, fourth, and fifth embodiments, i.e., the room illumination Fa(t) and the RGB illumination Fb(t), exist. Similar to the third, fourth, and fifth embodiments, the timing controller 420 determines values of durations of illuminated measurement and unilluminated measurement, a time difference between the illuminated measurement and the unilluminated measurement, and a duration of the illumination of the excitation light Le based on the data Da of the periods fa and fb, and obtains, for each set, timing of the illumination of the excitation light Le, illuminated measurement, and unilluminated measurement based on the determined values.

In this example, according to the ninth and tenth aspects of the present invention, the time difference T4k between the illuminated measurement and the unilluminated measurement in each set is determined to be 0.15 sec, which is three times the period fb, and the duration T4j of each of the illuminated measurement and the unilluminated measurement is determined to be 0.02 sec, which is identical with the period fa. In addition, the duration T4r of the illumination of the excitation light Le is determined to be 0.01 sec, which is shorter than the duration T4j of the illuminated measurement.

Based on the above values of the time difference T4k and the durations T4j and T4r, the measurement condition setting unit 420 obtains the timing t41, t44 of the illuminated measurement, timing t42, t43 of the illumination of the excitation light Le, and timing t45, t46 of the unilluminated measurement for the first set of operations, and timing t41', t44' of the illuminated measurement, timing t42', t43' of the illumination of the excitation light Le, and timing t45', t46' of the unilluminated measurement for the second set of operations. The information on the timing t41 to t46, and t41' to t46' is supplied from the measurement condition setting unit 420 to the timing controller 430, and is then converted into the aforementioned control signals for controlling the light source 320 and the measurement unit 330. When the control signals are supplied to the light source 320 and the measurement unit 330, the following operations are performed.

In the first set of operations, the illuminated measurement is performed for the duration T4j of 0.02 sec continuing from time t41 to t44, and the specimen 310 is illuminated with the excitation light Le for the duration T4r of 0.01 sec continuing from time t42 to time t43 during the illuminated measurement. Thus, a spectral distribution SP4c, which includes a spectral distribution of fluorescent light Ke emitted in response to the illumination of the excitation light Le, a spectral distribution of the room illumination Fa(t), and a spectral distribution of the RGB illumination Fb(t), is detected by the measurement unit 330. On the other hand, the unilluminated measurement is performed for the duration T4j of 0.02 sec continuing from time t45 to t46, and thus a spectral distribution SP4s, which includes a spectral distribution of the room illumination Fa(t), and a spectral distribution of the RGB illumination Fb(t), is detected by the measurement unit 330.

Similarly, in the second set of operations, the illuminated measurement is performed for the duration T4j of 0.02 sec continuing from time t41' to t44', and the specimen 310 is illuminated with the excitation light Le for the duration T4r of 0.01 sec continuing from time t42' to time t43' during the illuminated measurement. Thus, a spectral distribution SP4c', which includes a spectral distribution of fluorescent light Ke emitted in response to the illumination of the excitation light Le, a spectral distribution of the room illumination Fa(t), and a spectral distribution of the RGB illumination Fb(t), is detected by the measurement unit 330. On the other hand, the unilluminated measurement is performed for the duration T4j of 0.02 sec continuing from time t45' to t46', and thus a spectral distribution SP4s', which includes a spectral distribution of the room illumination Fa(t) and a spectral distribution of the RGB illumination Fb(t), is detected by the measurement unit 330.

Therefore, in the first set of operations, it is possible to obtain a true spectral distribution SP4k of the fluorescent light Ke which does not include the above spectral distribution of the room illumination Fa(t) and the spectral distributions of the RGB illumination Fb(t), by subtracting the spectral distributions SP4s from the spectral distribution SP4c. In addition, in the second set of operations, it is possible to obtain another true spectral distribution SP4k' of the fluorescent light Ke which does not include the above spectral distribution of the room illumination Fa(t) and the spectral distributions of the RGB illumination Fb(t), by subtracting the spectral distributions SP4s' and the spectral distribution SP4c'. That is, a total spectral distribution SP4k+SP4k' of the fluorescent light Ke which does not include the above spectral distribution of the room illumination Fa(t) and the spectral distributions of the RGB illumination Fb(t) is obtained as $$SP4k+SP4k'=(SP4c+SP4c')-(SP4s+SP4s').$$

Although two sets of illuminated measurement and unilluminated measurement are performed in the sixth embodiment, more than two sets of illuminated measurement and unilluminated measurement may be performed.

Operations of Seventh Embodiment

FIG. 12 is a timing chart of the operations in the seventh embodiment, which realizes the fifth and sixth aspects of the present invention. In the seventh embodiment, two sets of illuminated measurement and unilluminated measurement are performed, and the operations in each set are similar to the operations in the third embodiment.

In the example of FIG. 12, it is also assumed that the same types of background light as the third, fourth, and fifth embodiments, i.e., the room illumination Fa(t) and the RGB illumination Fb(t), exist. Similar to the third, fourth, fifth, and sixth embodiments, the timing controller 420 determines values of durations of illuminated measurement and unilluminated measurement, a time difference between the illuminated measurement and the unilluminated measurement, and a duration of the illumination of the excitation light Le based on the data Da of the periods fa and fb, and obtains, for each set, timing of the illumination of the excitation light Le, illuminated measurement, and unilluminated measurement based on the determined values.

According to the fifth and sixth aspects of the present invention, the time difference T5k between the illuminated measurement and the unilluminated measurement in each set is determined to be equal to an integer multiple of the least common multiple of the periods fa and fb. In this example, the time difference T5k is determined to be 0.2 sec, which is twice the least common multiple (0.1 sec) of the period fa(=0.02 sec) and the period fb(=0.05 sec). In addition, the duration T5j of each of the illuminated measurement and the unilluminated measurement is determined to be 0.01 sec, which is shorter than the above time difference T5k, and the duration T5r of the illumination of the excitation light Le is determined to be 0.005 sec, which is shorter than the duration T5j.

Based on the above values of the time difference T5k and the durations T5j and T5r, the measurement condition setting unit 420 obtains timing t51, t54 of the illuminated measurement, timing t52, t53 of the illumination of the excitation light Le, and timing t55, t56 of the unilluminated measurement for the first set of operations, and timing t51', t54' of the illuminated measurement, timing t52', t53' of the illumination of the excitation light Le, and timing t55', t56' of the unilluminated measurement for the second set of operations. The information on the timing t51 to t56, and t51' to t56' is supplied from the measurement condition setting unit 420 to the timing controller 430, and is then converted into the aforementioned control signals for controlling the light source 320 and the measurement unit 330. When the control signals are supplied to the light source 320 and the measurement unit 330, the following operations are performed.

In the first set of operations, the illuminated measurement is performed for the duration T5j of 0.01 sec continuing from time t51 to t54, and the specimen 310 is illuminated with the excitation light Le for the duration T5r of 0.01 sec continuing from time t52 to time t53 during the illuminated measurement. In the illuminated measurement of the first set, a spectral distribution SP5c is detected by the measurement unit 330, where the spectral distribution SP5c is a sum of a spectral distribution of fluorescent light Ke emitted in response to the illumination of the excitation light Le, a spectral distribution of the room illumination Fa(t), and a spectral distribution of the RGB illumination Fb(t). On the other hand, the unilluminated measurement is performed for the duration T5$j$ of 0.01 sec continuing from time t55 to t56. In the unilluminated measurement of the first set, a spectral distribution SP5$s$ is detected by the measurement unit 330, where the spectral distribution SP5$s$ is a sum of a spectral distribution of the room illumination Fa(t), and a spectral distribution of the RGB illumination Fb(t).

Similarly, in the second set of operations, the illuminated measurement is performed for the duration T5$j$ of 0.2 sec continuing from time t51' to t54', and the specimen 310 is illuminated with the excitation light Le for the duration T5$r$ of 0.01 sec continuing from time t52' to time t53' during the illuminated measurement. In the illuminated measurement of the second set, a spectral distribution SP5$c$' is detected by the measurement unit 330, where the spectral distribution SP5$c$' is a sum of a spectral distribution of fluorescent light Ke emitted in response to the illumination of the excitation light Le, a spectral distribution of the room illumination Fa(t), and a spectral distribution of the RGB illumination Fb(t). On the other hand, the unilluminated measurement is performed for the duration T5$j$ of 0.2 sec continuing from time t55' to t56'. In the unilluminated measurement of the second set, a spectral distribution SP5$s$' is detected by the measurement unit 330, where the spectral distribution SP5$s$' is a sum of a spectral distribution of the room illumination Fa(t), and a spectral distribution of the RGB illumination Fb(t).

Therefore, similar to the sixth embodiment, as a result of the first set of operations, it is possible to obtain a true spectral distribution SP5$k$ of the fluorescent light Ke which does not include the above spectral distribution of the room illumination Fa(t) and the spectral distributions of the RGB illumination Fb(t), as a difference between the spectral distributions SP5$c$ and the spectral distribution SP5$s$. In addition, as a result of the second set of operations, it is possible to obtain another true spectral distribution SP5$k$' of the fluorescent light Ke which does not include the above spectral distribution of the room illumination Fa(t) and the spectral distributions of the RGB illumination Fb(t), by subtracting the spectral distributions SP5$s$' from the spectral distribution SP5$c$'. That is, a total spectral distribution SP5$k$+SP5$k$' of the fluorescent light Ke which does not include the above spectral distribution of the room illumination Fa(t) and the spectral distributions of the RGB illumination Fb(t) is obtained as $$SP5k+SP5k'=(SP5c+SP5c')-(SP5s+SP5s').$$

Although two sets of illuminated measurement and unilluminated measurement are performed in the seventh embodiment, more than two sets of illuminated measurement and unilluminated measurement may be performed.

It is preferable to set the timing of the illuminated measurement and the unilluminated measurement to be in the vicinity of a certain phase of the cyclic variation of one of the room illumination Fa(t) and the RGB illumination Fb(t) which has a shorter period than the other, where the intensity of that one of the room illumination Fa(t) and the RGB illumination Fb(t) is minimized in the certain phase. For example, in FIG. 12, the period fa of the room illumination Fa(t) is shorter than the period fb of the RGB illumination Fb(t), and each of the illuminated measurement and the unilluminated measurement is performed for a duration which includes at its center a phase in which the intensity of the room illumination Fa(t) is minimized. In this case, the influence of the background light can be eliminated further effectively.

Variations of Third to Seventh Embodiments (1) Although each duration of the illuminated measurement and the unilluminated measurement includes only one duration of the illumination of the excitation light Le in the aforementioned third to seventh embodiments, each duration of the illuminated measurement and the unilluminated measurement may include more than one duration of the illumination of the excitation light Le.

(2) Although only two types of background light exist in the aforementioned third to seventh embodiments, operations similar to those performed in the aforementioned third to seventh embodiments can be performed when more than two types of background light exist. For example, when seven types of background light, F1($t$), F2($t$), F3($t$), F4($t$), F5($t$), F6($t$), and F7($t$) exist, the seven types of background light can be deemed to be two types of background light by combining three types of background light F1($t$), F2($t$), and F3($t$) into one type of background light FX(t), and the other types of background light F4($t$), F5($t$), F6($t$), and F7($t$) into another type of background light FY(t). Therefore, when periods fx and fy of the background light FX(t) and FY(t) are obtained, the operations similar to those performed in the aforementioned third to seventh embodiments can be performed.

Other Matters

The present invention can be applied to spectrum analyzers, quantitative analyzers, image measurement apparatuses, and the like which perform measurement of fluorescence, phosphorescence, absorption, or the like.

In addition, all of the contents of the Japanese Patent Application Nos. 11(1999)-33741 and 11(1999)-239095 are incorporated into this specification by reference.

What is claimed is:

1. An optical measurement method for performing measurement of first light, which has been emitted from or reflected by a specimen, or has penetrated through the specimen, under background light having intensity which varies cyclically with a period, said method comprising steps of:
   (a) performing a first operation of measuring the first light for a first duration having a certain length and beginning at a first time, while illuminating the specimen with second light, to obtain a first measurement result;
   (b) performing a second operation of measuring the first light for a second duration having the same length as the first duration and beginning at a second time which is different from said first time by an integer multiple of said period, while illumination of the specimen is stopped, to obtain a second measurement result; and
   (c) subtracting said second measurement result from said first measurement result, to obtain a third measurement result which is not affected by said background light.

2. An optical measurement method according to claim 1, further comprising an additional step of obtaining said period by measuring the intensity of the background light.

3. An optical measurement apparatus for performing measurement of first light, which has been emitted from or reflected by a specimen, or has penetrated through the specimen, under background light having intensity which varies cyclically with a period, said apparatus comprising:
   a first measurement unit which performs a first operation of measuring the first light while illuminating the specimen with second light, to obtain a first measurement result;

a second measurement unit which performs a second operation of measuring the first light while illumination of the specimen is stopped, to obtain a second measurement result;

a control unit which controls timing of the operations of the first and second measurement units so that said first operation is performed for a first duration having a certain length and beginning at a first time, and said second operation is performed for a second duration having the same length as the first duration and beginning at a second time which is different from said first time by an integer multiple of said period; and a calculation unit which obtains a third measurement result, which is not affected by said background light, by subtracting said second measurement result from said first measurement result.

4. An optical measurement apparatus according to claim 3, further comprising an additional unit which obtains said period by measuring the intensity of the background light.

5. An optical measurement method for performing measurement of first light, which has been emitted from or reflected by a specimen, or has penetrated through the specimen, under background light having intensity which varies cyclically with a period, said method comprising steps of:

(a) performing a first operation of measuring the first light for a first duration having a length equal to an integer multiple of said period, while illuminating the specimen with second light, to obtain a first measurement result;

(b) performing a second operation of measuring the first light for a second duration having a length equal to the length of the first duration, while illumination of the specimen is stopped, to obtain a second measurement result; and (c) subtracting said second measurement result from said first measurement result, to obtain a third measurement result which is not affected by said background light.

6. An optical measurement method according to claim 5, further comprising an additional step of obtaining said period by measuring the intensity of the background light.

7. An optical measurement apparatus for performing measurement of first light, which has been emitted from or reflected by a specimen, or has penetrated through the specimen, under background light having an intensity which varies cyclically with a period, said apparatus comprising:

a first measurement unit which performs a first operation of measuring the first light while illuminating the specimen with second light, to obtain a first measurement result;

a second measurement unit which performs a second operation of measuring the first light while illumination of the specimen is stopped, to obtain a second measurement result;

a control unit which controls timing of the operations of the first and second measurement units so that each of said first and second operations is performed for a duration having an identical length equal to an integer multiple of said period; and a calculation unit which obtains a third measurement result, which is not affected by said background light, by subtracting said second measurement result from said first measurement result.

8. An optical measurement apparatus according to claim 7, further comprising an additional unit which obtains said period by measuring the intensity of the background light.

9. An optical measurement method for performing measurement of first light, which has been emitted from or reflected by a specimen, or has penetrated through the specimen, under a plurality of types of background light respectively having a plurality of different periods with which intensities of the plurality of types of background light vary cyclically, said method comprising steps of:

(a) performing a first operation of measuring the first light for a first duration having a length equal to an integer multiple of a least common multiple of said plurality of different periods, while illuminating the specimen with second light, to obtain a first measurement result;

(b) performing a second operation of measuring the first light for a second duration having a length equal to the length of the first duration, while illumination of the specimen is stopped, to obtain a second measurement result; and (c) subtracting said second measurement result from said first measurement result, to obtain a third measurement result which is not affected by said plurality of types of background light.

10. An optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically, said apparatus comprising:

a first measurement unit which performs a first operation of measuring the first light while illuminating the specimen with second light, to obtain a first measurement result;

a second measurement unit which performs a second operation of measuring the first light while illumination of the specimen is stopped, to obtain a second measurement result;

a control unit which controls timing of the operations of the first and second measurement units so that each of said first and second operations is performed for a duration having an identical length equal to an integer multiple of a least common multiple of said plurality of different periods; and a calculation unit which obtains a third measurement result, which is not affected by said plurality of types of background light, by subtracting said second measurement result from said first measurement result.

11. An optical measurement method for performing measurement of first light, which has been emitted from or reflected by a specimen, or has penetrated through the specimen, under a plurality of types of background light respectively having a plurality of different periods with which intensities of the plurality of types of background light vary cyclically, said method comprising steps of:

(a) performing a first operation of measuring the first light for a first duration having a certain length and beginning at a first time while illuminating the specimen with second light, to obtain a first measurement result;

(b) performing a second operation of measuring the first light for a second duration having the same length as the first duration and beginning at a second time which is different from said first time by an integer multiple of a least common multiple of said plurality of different periods, while illumination of the specimen is stopped, to obtain a second measurement result; and (c) subtracting said second measurement result from said first measurement result, to obtain a third measurement result which is not affected by said plurality of types of background light.

12. An optical measurement method according to claim 11, wherein each of said first and second operations is performed a plurality of times.

13. An optical measurement method according to claim 11, wherein each of said first and second operations is performed in synchronization with one of the plurality of different periods of a selected one of the plurality of types of background light.

14. An optical measurement method according to claim 13, wherein each of said first and second operations is performed in the vicinity of a certain phase of said one of the plurality of different periods, where the intensity of the selected one of the plurality of types of background light is minimized in said certain phase.

15. An optical measurement method according to claim 13, wherein said one of the plurality of different periods is a minimum period of the plurality of different periods.

16. An optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically, said apparatus comprising:
- a first measurement unit which performs a first operation of measuring the first light while illuminating the specimen with second light, to obtain a first measurement result;
- a second measurement unit which performs a second operation of measuring the first light while illumination of the specimen is stopped, to obtain a second measurement result;
- a control unit which controls timing of the operations of the first and second measurement units so that said first operation is performed for a first duration having a certain length and beginning at a first time, and said second operation is performed for a second duration having the same length as the first duration and beginning at a second time which is different from said first time by an integer multiple of a least common multiple of said plurality of different periods; and
- a calculation unit which obtains a third measurement result, which is not affected by said plurality of types of background light, by subtracting said second measurement result from said first measurement result.

17. An optical measurement apparatus according to claim 16, wherein each of said first and second operations is performed a plurality of times.

18. An optical measurement apparatus according to claim 16, wherein each of said first and second operations is performed in synchronization with one of the plurality of different periods of a selected one of the plurality of types of background light.

19. An optical measurement apparatus according to claim 18, wherein each of said first and second operations is performed in the vicinity of a certain phase of said one of the plurality of different periods, where the intensity of the selected one of the plurality of types of background light is minimized in said certain phase.

20. An optical measurement apparatus according to claim 18, wherein said one of the plurality of different periods is a minimum period of the plurality of different periods.

21. An optical measurement method for performing measurement of first light, which has been emitted from or reflected by a specimen, or has penetrated through the specimen, under a plurality of types of background light respectively having a plurality of different periods with which intensities of the plurality of types of background light vary cyclically, said method comprising steps of:
- (a) performing a first operation of measuring the first light for a first duration beginning at a first time and having a length equal to an integer multiple of a least common multiple of at least one period among said plurality of different periods, while illuminating the specimen with second light, to obtain a first measurement result;
- (b) performing a second operation of measuring the first light for a second duration having the same length as the first duration and beginning at a second time which is different from said first time by an integer multiple of a least common multiple of said plurality of different periods other than said at least one period, while illumination of the specimen is stopped, to obtain a second measurement result; and
- (c) subtracting said second measurement result from said first measurement result, to obtain a third measurement result which is not affected by said plurality of types of background light.

22. An optical measurement method according to claim 21, wherein each of said first and second operations is performed a plurality of times.

23. An optical measurement method according to claim 21, wherein each of said first and second operations is performed in synchronization with a selected one of said plurality of different periods other than said at least one period.

24. An optical measurement method according to claim 23, wherein each of said first and second operations is performed in the vicinity of a certain phase of said selected one of said plurality of different periods other than said at least one period, where the intensity of the selected one of the plurality of types of background light is minimized in said certain phase.

25. An optical measurement method according to claim 23, wherein said selected one of said plurality of different periods other than said at least one period is a minimum period of the plurality of different periods other than the at least one period.

26. An optical measurement apparatus for performing measurement of first light, which has been emitted from or reflected by a specimen, or has penetrated through the specimen, under a plurality of types of background light respectively having a plurality of different periods with which intensities of the plurality of types of background light vary cyclically, said apparatus comprising:
- a first measurement unit which performs a first operation of measuring the first light while illuminating the specimen with second light, to obtain a first measurement result;
- a second measurement unit which performs a second operation of measuring the first light while illumination of the specimen is stopped, to obtain a second measurement result;
- a control unit which controls timing of the operations of the first and second measurement units so that said first operation is performed for a first duration beginning at a first time and having a length equal to an integer multiple of a least common multiple of at least one period among said plurality of different periods, and said second operation is performed for a second duration having the same length as the first duration and beginning at a second time which is different from said first time by an integer multiple of a least common multiple of said plurality of different periods other than said at least one period; and a calculation unit which obtains a third measurement result, which is not affected by said plurality of types of background light, by subtracting said second measurement result from said first measurement result.

27. An optical measurement apparatus according to claim 26, wherein each of said first and second operations is performed a plurality of times.

28. An optical measurement apparatus according to claim 26, wherein each of said first and second operations is performed in synchronization with a selected one of said plurality of different periods other than said at least one period.

29. An optical measurement apparatus according to claim 28, wherein each of said first and second operations is performed in the vicinity of a certain phase of said selected one of said plurality of different periods other than said at least one period, where the intensity of the selected one of the plurality of types of background light is minimized in said certain phase.

30. An optical measurement apparatus according to claim 28, wherein said selected one of said plurality of different periods other than said at least one period is a minimum period of the plurality of different periods other than the at least one period.

* * * * *